US008637021B2

(12) United States Patent
Del Rio et al.

(10) Patent No.: US 8,637,021 B2
(45) Date of Patent: Jan. 28, 2014

(54) FORMULATIONS FOR TACI-IMMUNOGLOBULIN FUSION PROTEINS

(75) Inventors: Alessandra Del Rio, Rome (IT); Gianluca Rinaldi, Monterotondo (IT); Joel Richard, Mèrè (FR)

(73) Assignee: Ares Trading S.A. (CH)

( * ) Notice: Subject to any disclaimer, the term of this patent is extended or adjusted under 35 U.S.C. 154(b) by 102 days.

(21) Appl. No.: 12/740,845

(22) PCT Filed: Nov. 12, 2008

(86) PCT No.: PCT/EP2008/065395
§ 371 (c)(1),
(2), (4) Date: Aug. 3, 2010

(87) PCT Pub. No.: WO2009/062960
PCT Pub. Date: May 22, 2009

(65) Prior Publication Data
US 2010/0297122 A1    Nov. 25, 2010

Related U.S. Application Data

(60) Provisional application No. 61/003,028, filed on Nov. 14, 2007, provisional application No. 61/002,988, filed on Nov. 14, 2007, provisional application No. 61/072,038, filed on Mar. 27, 2008.

(30) Foreign Application Priority Data

Nov. 12, 2007  (EP) .................................. 07120489
Nov. 12, 2007  (EP) .................................. 07120490
Mar. 27, 2008  (EP) .................................. 08005923

(51) Int. Cl.
*A61K 39/395*    (2006.01)
(52) U.S. Cl.
USPC .................. 424/134.1; 424/158.1; 530/387.3
(58) Field of Classification Search
None
See application file for complete search history.

(56) References Cited

U.S. PATENT DOCUMENTS

| | | | |
|---|---|---|---|
| 6,171,586 B1 * | 1/2001 | Lam et al. .................. | 424/130.1 |
| 2002/0086018 A1 * | 7/2002 | Theill et al. ................ | 424/146.1 |
| 2003/0103986 A1 * | 6/2003 | Rixon et al. ............... | 424/178.1 |
| 2006/0067933 A1 | 3/2006 | Gross et al. | |

FOREIGN PATENT DOCUMENTS

| WO | WO 01/60397 A | 8/2001 |
|---|---|---|
| WO | WO 02/094852 A | 11/2002 |
| WO | WO 2007/059188 A | 5/2007 |

OTHER PUBLICATIONS

Lins et al, Proteins:Structure, Function, and Bioinformatics, 55:177-186, 2004.*

Jain et al, Protein Science, 18:24-36, 2009.*
Altschul, Stephen F., et al., "Basic Local Alignment Search Tool", *J. Mol. Biol.*, vol. 215, (1990), pp. 403-410.
Altschul, Stephen F., et al., "Gapped BLAST and PSI-BLAST: A New Generation of Protein Database Search Programs", *Nucleic Acids Research*, vol. 25, No. 17, (1997), pp. 3389-3402.
Armour, Kathryn L., et al., "Recombinant Human IgG M molecules Lacking Fcγ Receptor I Binding and Monocyte Triggering Activities", *Eur. J. Immunol.*, vol. 29, (1999), pp. 2613-2624.
Cheema, Gurtej S., et al., "Elevated Serum B Lymphocyte Simulator Levels in Patients with Systemic Immune-Based Rheumatic Diseases", *Arthritis & Rheumatism*, vol. 44, No. 6, (Jun. 2001), pp. 1313-1319.
Devereux, John et al., "A Comprehensive Set of Sequence Analysis Programs for the VAX", *Nucleic Acids Research*, vol. 12, No. 1 (1984), pp. 387-395.
Do, Richard K.G., et al., "Attenuation of Apoptosis Underlies B Lymphocyte Stimulator Enhancement of Humoral Immune Response", *J. Exp. Med.*, vol. 192, No. 7 (Oct. 2, 2000), pp. 953-964.
Duncan, Alexander R., et al., "Localization of the Binding Site for the Human High-Affinity FC Receptor on IgG", *Nature*, No. 7 (Apr. 1988), pp. 563-564.
Grantham, R., "Amino Acid Difference Formula to Help Explain Protein Evolution", *Science*, vol. 185 (1974), pp. 862-864.
Groom, J., et al., "Association of BAFF/BLys Overexpression and Altered B Cell Differentiation with Sjögren's Syndrome", *The Journal of Clinical Investigation*, vol. 109, No. 1 (Jan. 2002), pp. 59-68.
Gross, Jane A., et al., TACI and BCMA are Receptors for a TNF Homologue Implicated in B-Cell Autoimmune Disease, *Nature*, vol. 404 (Apr. 2000), pp. 995-999.
Horton, Robert M., et al., "Engineering Hybrid Genes Without the Use of Restriction Enzymes: Gene Splicing by Overlap Extension", *Gene*, vol. 77 (1989).
Kabat, Elvin A., et al., "Quantitative Estimation of the Albumin and Gamma Globulin in Normal and Pathologic Cerebrospinal Fluid by Immunochemical Methods", *American Journal of Medicine*, vol. 4 (1948), pp. 653-662.
Kallad, Susan L., "The Role of BAFF in Immune Function and Implications for Autoimmunity", *Immunological Reviews*, vol. 204 (2005), pp. 43-54.
Mackay, Fabienne, et al., "Mice Transgenic for BAFF Develop Lymphocytic Disorders Along with Autoimmune Manifestations", *J. Exp. Med.*, vol. 190, No. 11 (Dec. 9, 1999), pp. 1697-1710.
Mariette, X., et al., "The Level of BLyS (BAFF) Correlates with the Tirte of Autoantibodies in Human Sjögren's Syndrome", *Ann. Rheum. Dis.*, vol. 62 (2003), pp. 168-171.
Marsters, Scot A., et al., "Interaction of the TNF Homologues BLyS and APRIL with the TNF Receptor Homologues BCMA and TACT", *Curr. Biol.*, (2000) vol. 10, No. 13, pp. 785-788.
Moore, Paul A., et al., "BLyS: Member of the Tumor Necrosis Factor Family and B Lymphocyte Stimulator", *Science*, vol. 285, (Jul. 9, 1999), pp. 260-263.
Pearson, William R., "Rapid and Sensitive Sequence Comparison with FASTP and FASTA", *Methods in Enzymology*, vol. 183, (1990), pp. 63-98.

(Continued)

*Primary Examiner* — Patricia A Duffy
(74) *Attorney, Agent, or Firm* — Alston & Bird LLP

(57) ABSTRACT

The invention relates to formulations of TACI-Immunoglobulin fusion proteins.

21 Claims, No Drawings

(56) References Cited

OTHER PUBLICATIONS

Roschke, Viktor, et al., "BLyS and APRIL form Biologically Active Heterotrimers that are Expressed in Patients with Systemic Immune-Based Diseases", *The Journal of Immunology*, vol. 169 (2002), pp. 4314-4321.

Rudick, R.A., et al. "Use of the Multiple Sclerosis Functional Composite to Predict Disability in Relapsing MS", *Neurology*, vol. 56 (2001), p. 1324-1330.

Schneider, Pascal, et al., "BAFF, A Novel Ligand of the Tumor Necrosis Factor Family, Stimulates B Cell Growth", *J. Exp. Med.*, vol. 189, No. 11 (Jun. 7, 1999), p. 1747-1756.

Shields, Robert L., et al., "High Resolution Mapping of the Binding Site on Human IgG1 for FcγRI, FcγRIII, and FcRn and Design of IgG1 Variants with Improved Binding to the FcγR", *The Journal of Biological Chemistry*, vol. 276, No. 9 (Mar. 2, 2001), pp. 6591-6604.

Söderström, Mats, et al., "Optic Neuritis and Multiple Sclerosis", *Neurology*, vol. 43 (Jun. 1993), pp. 1215-1222.

Sondermann, Peter, et al., "The 3.2-A Crystal Structure of the Human IgG1 Fc Fragment—FcγRIII Complex", *Nature*, vol. 406 (Jul. 20, 2000), pp. 267-273.

Tao, Mi-Hua et al., "Structural Features of Human Immunoglobulin G that Determine Isotype-Specific Differences in Complement Activation", *J. Exp. Med.*, vol. 178, (Aug. 1993), pp. 661-667.

Thangarajh, Mathula, et al., "Expression of B-Cell-Activating Factor of the TNF Family (BAFF) and its Recepors in Multiple Sclerosis", *Journal of Neuroimmunology*, vol. 152 (2002), pp. 183-190.

Thompson, Jeffrey S., et al., "BAFF-R, A Newly Indentified TNF Receptor that Specifically Interacts with BAFF", *Science*, vol. 293 (Sep. 14, 2001), pp. 2108-2111.

Urlaub, Gail, et al., "Effect of Gamma Rays at the Dihydrofolate Reductase Locus: Deletions and Inversions", *Somatic Cell and molecular Genetics*, vol. 12, No. 6, (1986), pp. 555-566.

Wines, Bruce D., et al., "The IgG Fc Contains Distinct Fc Receptor (FcR) Binding Sites: The Leukocyte Receptors FcγRi and FcγRIIa Bind to a region in the Fc Distinct from that Recognized by Neonatal FcR and Protein A", *The Journal of Immunology*, vol. 164 (2000), pp. 5313-5318.

* cited by examiner

FORMULATIONS FOR TACI-IMMUNOGLOBULIN FUSION PROTEINS

CROSS-REFERENCE TO RELATED APPLICATIONS

This application is a 35 U.S.C. 371 entry of PCT application no. PCT/EP2008/065395 filed on Nov. 12, 2008 which claims priority of EP07120489.5, filed Nov. 12, 2007, EP07120490.3, filed Nov. 12, 2007, EP08005923.1, filed Mar. 27, 2008, U.S. Provisional Application Nos. 61/003,028, filed on Nov. 14, 2007, 61/002,988 filed Nov. 14, 2007 and 61/072,038, filed Mar. 27, 2008, each of which is herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named 388713seqlist.txt, created on Apr. 30, 2010, and having a size of 52 KB and is filed concurrently with the specification. The sequence listing contained in this ASCII formatted document is part of the specification and is herein incorporated by reference in its entirety.

FIELD OF INVENTION

The present invention is in the field of formulations for therapeutic proteins. More specifically, it relates to formulations for TACI-immunoglobulin (Ig) fusion proteins having a pH ranging from 4.5 to 5.5.

BACKGROUND OF THE INVENTION

The BLyS Ligand/Receptor Family

Three receptors, TACI (transmembrane activator and CAML-interactor), BCMA (B-cell maturation antigen) and BAFF-R (receptor for B-cell activating factor), have been identified that have unique binding affinities for the two growth factors BlyS (B-lymphocyte stimulator) and APRIL (a proliferation-inducing ligand) (Marsters et al. 2000; Thompson et al. 2001).

TACI and BCMA bind both BLyS and APRIL, while BAFF-R appears capable of binding only BLyS with high affinity (Marsters et al., 2000; Thompson et al. 2001). As a result, BLyS is able to signal through all three receptors, while APRIL only appears capable of signaling through TACI and BCMA. In addition, circulating heterotrimeric complexes of BLyS and APRIL (groupings of three protein subunits, containing one or two copies each of BLyS and APRIL subunits) have been identified in serum samples taken from patients with systemic immune-based rheumatic diseases, and have been shown to induce B-cell proliferation in vitro (Roschke et al., 2002).

BLyS and APRIL are potent stimulators of B-cell maturation, proliferation and survival (Moore et al., 1999; Schneider et al., 1999; Do et al., 2000). BLyS and APRIL may be necessary for persistence of autoimmune diseases, especially those involving B-cells. Transgenic mice engineered to express high levels of BLyS exhibit immune cell disorders and display symptoms similar to those seen in patients with Systemic Lupus Erythematosus (Gross et al. 2000; Mackay et al. 1999). Similarly, increased levels of BLyS/APRIL have been measured in serum samples taken from Systemic Lupus Erythematosus patients and other patients with various autoimmune diseases like Rheumatoid Arthritis (Roschke 2002; Cheema et al. 2001; Groom et al. 2002), extending the association of BLyS and/or APRIL and B-cell mediated diseases from animal models to humans. The expression of BLyS and APRIL are upregulated in peripheral blood monocytes and T cells of MS patients (Thangarajh et al., 2004; Thangarajh et al., 2005). In MS lesions, BLyS expression was found strongly upregulated on astrocytes localized close to immune cells expressing BAFF-R (Krumbholz et al., 2005).

Atacicept

Atacicept (INN) is a recombinant fusion protein containing the extracellular, ligand-binding portion of the receptor TACI (Transmembrane activator and calcium modulator and cyclophilin-ligand (CAML)-interactor) and the modified Fc portion of human IgG. Atacicept acts as an antagonist to BLyS (B-lymphocyte stimulator) and APRIL (A proliferation-inducing ligand), both members of the tumor necrosis factor (TNF) superfamily. BLyS and APRIL have been shown to be important regulators of B cell maturation function and survival.

Atacicept is a soluble glycoprotein containing 313 amino acids, resulting from the fusion of a human $IgG_1$-Fc and a portion from the extracellular domain of the BLyS receptor TACI, with a predicted mass of 35.4 kilodalton (kDa). The product conformation is dimeric, with a predicted mass of 73.4 kDa. Atacicept is produced in Chinese Hamster Ovary (CHO) cells by recombinant technology.

In atacicept, the human $IgG_1$-Fc was modified to reduce Fc binding to the C1q component of complement and the interaction with antibody receptors (Tao et al., 1993; Canfield et al., 1991). Atacicept was tested and confirmed for reduction of these Fc effector functions.

Formulations of Therapeutic Proteins

TACI-Ig fusion proteins such as atacicept, are biologicals, i.e. therapeutic proteins for treatment of human diseases and hence for human administration.

Formulations are developed in order to support the successful delivery of therapeutic proteins. Problems frequently encountered in the context of therapeutic proteins are e.g. poor stability of the protein (storage in refrigerator or freezer is often necessary), poor bioavailability, and patient unfriendly dosage forms, usually in the parenteral route.

In biotechnological production processes, therapeutic proteins are generally obtained in a highly purified form in aqueous solution. When formulating these protein solutions, e.g., for parenteral delivery, stabilization of the protein is important. Therefore, excipients that stabilize the protein have to be chosen. The stability of highly purified proteins in solution can also be affected by the buffer. Buffers affect the stability of a protein in solution both by the ionic strength and the pH of the solution. Examples of buffers that have been used for this purpose are phosphate, citrate, maleate and succinate buffers.

Even if the therapeutic protein is in solution at the start of its shelf life, the challenge is to maintain the protein in solution and prevent aggregation during storage, leading to formation of particulates or precipitation, and prevention of degradation (e.g. by hydrolysis, oxidation, deamidation, truncation, or denaturation).

Temperature also influences the solubility. Normally, the solubility increases with the temperature. However, above a certain temperature threshold, the protein may partly unfold leading to decreased solubility or aggregation/precipitation.

In order to prevent aggregation and degradation, and in order to obtain a drug that is stable over an extended period of time, a formulation containing one or more excipients which stabilize the protein therapeutic needs to be developed.

The present invention addresses the need of a stable and pharmaceutically acceptable formulation for TACI-immunoglobulin fusion proteins, which are used as therapeutic proteins for the treatment of human disease.

SUMMARY OF THE INVENTION

The present invention is based on the development of stable formulations for TACI-immunoglobulin fusion proteins.

In a first aspect, the formulation of the invention comprises:
a) TACI-immunoglobulin (TACI-Ig) fusion protein comprising
  i. the TACI extracellular domain or a fragment or variant thereof which binds to BlyS and/or APRIL; and
  ii. an immunoglobulin-constant domain; and
b) a buffer buffering the formulation at a pH ranging between 4.5 and 5.5.

In a second aspect, the invention relates to a pharmaceutical composition comprising such a formulation.

A third aspect of the invention relates to the formulation or the pharmaceutical composition of the invention for treatment or prevention of an autoimmune disease or a lymphoproliferative disorder.

In a fourth aspect, the invention relates to a process for the preparation of a formulation in accordance with the invention, comprising the step of preparing a liquid solution of the TACI-Ig fusion protein and adjusting the pH of said liquid solution to a pH ranging from 4.5 to 5.5.

A fifth aspect of the invention relates to a process for preparation of a formulation in accordance with the invention, comprising the step of filling a predetermined amount of the formulation into a sterile container.

DETAILED DESCRIPTION OF THE INVENTION

The present invention is based on the development of a formulation for TACI-immunoglobulin (TACI-Ig) fusion proteins, in which the TACI-Ig fusion protein is stable over an extended period of time (e.g. more than 3 months, more than 6 months, more than 12 months, more than 15 months or more than 18 months).

In accordance with the present invention, the formulation comprises:
a) TACI-immunoglobulin (TACI-Ig) fusion protein comprising
  i. the TACI extracellular domain or a fragment or variant thereof which binds to BlyS and/or APRIL; and
  ii. an immunoglobulin-constant domain;
b) a buffer buffering the formulation at a pH ranging between 4.5 and 5.5.

In an embodiment of the formulation of the invention, the pH of the formulation has a pH ranging from 4.7 to 5.3 and more preferably from 4.9 to 5.1.

The formulation can thus e.g. have a pH of 4.5, 4.6, 4.7, 4.8, 4.9, 5.0, 5.1, 5.2, 5.3, 5.4 or 5.5. In a preferred embodiment, the pH of the formulation is 5.0.

The buffer used in the formulation of the invention can e.g. be phosphate, acetate, citrate, succinate or histidine buffer. The buffer can have a strength in the range of 1 to 50 mM, preferably 5 to 25 mM. For instance, the buffer comprised in the formulation of the invention can have a strength of 5, 6, 7, 8, 9, 10, 11, 12, 13, 14, 15, 16, 17, 18, 19, 20, 25, 30, 35, 40, 45 or 50 mM.

In a preferred embodiment of the formulation of the invention, the buffer is acetate buffer. Preferably, it is sodium acetate (Na-Acetate) buffer. In an embodiment of the invention, the buffer is 5 to 25 mM, preferably 8 to 12 mM, more preferably around 10 mM Na-acetate buffer.

In an embodiment, the formulation of the invention comprises an excipient. Suitable excipients are e.g. mannitol, sorbitol, glycine or trehalose. Mannitol or sorbitol can e.g. be present in the formulation at a concentration ranging from 30 to 80 or 40 to 60 or about 50 or 51 mg/mL. Glycine can e.g. be present in the formulation at a concentration ranging from 10 to 30 or preferably from 15 to 25, or 20 or 21 mg/mL.

Trehalose is a disaccharide (sugar) composed of two glucose molecules bound by an alpha, alpha-1,1 linkage. Trehalose, such as anhydrous trehalose, can e.g. be present in the formulation of the invention in a concentration ranging from 50 to 120 mg/mL or preferably 60 to 100 mg/mL. For instance, the formulation can comprise 70, 75, 80, 85, 90, 95, 100, 105, or 110 mg/mL trehalose. In a preferred embodiment, the formulation comprises about 80 mg/mL trehalose anhydrous.

Whilst the formulation of the invention can comprise an excipient or salt such as NaCl, $CaCl_2$, $MgCl_2$, it is preferred in the context of the present invention that the formulation is salt-free.

The formulation can further comprise a surfactant, such as e.g. Tween 20 or, preferably, Poloxamer 188 (Lutrol® or Pluronic® F68). In accordance with an embodiment of the invention, the formulation is free of a surfactant.

In an embodiment, the formulation of the invention further comprises a preservative. It is preferred to use benzyl alcohol in combination with benzalkonium chloride as a preservative. For instance, the formulation can comprise 0.1% to 0.5% benzyl alcohol, e.g. 0.2%, 0.3% or 0.4% benzyl alcohol and 0.0007% to 0.0015% benzalkonium chloride, e.g. 0.0008%, 0.0009%, 0.001%, 0.0011%, or 0.0012% benzalkonium chloride. In a highly preferred embodiment, the formulation comprises 0.3% benzyl alcohol in combination with 0.001% benzalkonium chloride.

The formulation of the present invention comprises TACI-immunoglobulin (TACI-Ig) fusion protein as the therapeutically active compound, i.e. as the active ingredient. Said TACI-Ig fusion protein comprises or consists of (a) the TACI extracellular domain or a variant or fragment thereof which binds to BlyS and/or APRIL; and (b) a immunoglobulin-constant domain. It is understood by the person skilled in the art that a TACI-Ig fusion protein to be formulated in accordance with the present invention is not an anti-TACI antibody. An anti-TACI antibody would not comprise the TACI extracellular domain or a variant or fragment thereof which binds to BlyS and/or APRIL, but would be directed against an epitope from the TACI extracellular domain.

In the frame of the present invention, the term "TACI extracellular domain" also refers to any variant thereof being at least 80% or 85%, preferably at least 90% or 95% or 99% identical to TACI extracellular domain (SEQ ID NO: 1). The term "TACI extracellular domain" also includes variants comprising no more than 50 or 40 or 30 or 20 or 10 or 5 or 3 or 2 or 1 conservative amino acid substitutions. Any such variant is able to bind BlyS and/or APRIL and/or any BlyS-APRIL heterotrimer. Preferably, such a variant also inhibits the biological activity of BlyS and/or of APRIL and/or of any BlyS/APRIL heterotrimer. The biological activity of BlyS or APRIL is e.g. B cell proliferation.

Fragments (active fragments) and variants of the TACI extracellular domain can be used in the context of the present invention as well, as long as the fragment is able to bind BlyS and/or APRIL and/or a BlyS-APRIL heterotrimer. Preferably, such a fragment also inhibits or reduces the biological activity of BlyS and/or of APRIL and/or of a BlyS/APRIL heterotrimer.

The ability of any TACI extracellular domain, TACI-Ig fusion protein, or any variant or fragment thereof to bind BlyS and/or APRIL and/or BLyS/APRIL heterotrimer can be assessed e.g. in accordance with Example 2 below. The ability to inhibit or reduce BlyS, APRIL or BlyS/APRIL heterotrimer biological activity can be assessed e.g. in accordance with Example 3 below.

It is preferred, in the context of the present invention, that any such fragment or variant of a TACI extracellular domain or a TACI-Ig fusion protein, does not have any biological activity which is significantly lower that that of atacicept, i.e. a protein having the amino acid sequence of SEQ ID NO: 3.

The term "immunoglobulin (Ig)-constant domain", as used herein, is also called an"Fc domain" and is derived from a human or animal immunoglobulin (Ig) that is preferably an IgG. The IgG may be an IgG1, IgG2, IgG3 or IgG4. The Fc domain preferably comprises at least the CH2, CH3 domain of IgG1, preferably together with the hinge region.

Preferably, the Ig constant domain is a human IgG1 domain.

In one embodiment, human IgG1 constant domain has been modified for reduced complement-dependent cytotoxicity (CDC) and/or antibody-dependent cellular cytotoxicity (ADCC).

In ADCC, the Fc domain of an antibody binds to Fc receptors (FcγRs) on the surface of immune effector cells such as natural killers and macrophages, leading to the phagocytosis or lysis of the targeted cells. In CDC, the antibodies kill the targeted cells by triggering the complement cascade at the cell surface. The binding of IgG to the activating (FcγRI, FcγRIIa, FcγRIIIa and FcγRIIIb) and inhibitory (FcγRIIb) FcγRs or the first component of complement (C1q) depends on residues located in the hinge region and the CH2 domain. Two regions of the CH2 domain are important for FcγRs and complement C1q binding, and have unique sequences in IgG2 and IgG$_4$. For instance, substitution of IgG2 residues at positions 233-236 into human IgG1 greatly reduced ADCC and CDC (Armour et al., 1999 and Shields et al., 2001). The following Fc mutations, according to EU index positions (Kabat et al., 1991), can e.g. be introduced into an Fc derived from IgG1:
T250Q/M428L
M252Y/S254T/T256E+H433K/N434F
E233P/L234V/L235A/ΔG236+A327G/A330S/P331S
E333A; K322A.

Further Fc mutations may e.g. be the substitutions at EU index positions selected from 330, 331 234, or 235, or combinations thereof. An amino acid substitution at EU index position 297 located in the CH2 domain may also be introduced into the Fc domain in the context of the present invention, eliminating a potential site of N-linked carbohydrate attachment. The cysteine residue at EU index position 220 may also be replaced with a serine residue, eliminating the cysteine residue that normally forms disulfide bonds with the immunoglobulin light chain constant region.

Particular Fc domains suitable for TACI-Ig fusion proteins to be used in accordance with the present invention have been prepared.

Specifically, six versions of a modified human IgG1 Fc were generated for creating Fc fusion proteins and are named Fc-488, as well as Fc4, Fc5, Fc6, Fc7, and Fc8. Fc-488 (having a DNA sequence of SEQ ID NO: 4 and an amino acid sequence of SEQ ID NO: 5) was designed for convenient cloning of a fusion protein containing the human γ1 Fc region, and it was constructed using the wild-type human immunoglobulin γ1 constant region as a template. Concern about potential deleterious effects due to an unpaired cysteine residue led to the decision to replace the cysteine that normally disulfide bonds with the immunoglobulin light chain constant region with a serine residue. An additional change was introduced at the codon encoding EU index position 218 to introduce a BglII restriction enzyme recognition site for ease of future DNA manipulations. These changes were introduced into the PCR product encoded on the PCR primers. Due to the location of the BglII site and in order to complete the Fc hinge region, codons for EU index positions 216 and 217 were incorporated in the fusion protein partner sequences. Fc4, Fc5, and Fc6 contain mutations to reduce effector functions mediated by the Fc by reducing FcγRI binding and complement C1q binding. Fc4 contains the same amino acid substitutions that were introduced into Fc-488. Additional amino acid substitutions were introduced to reduce potential Fc mediated effector functions. Specifically, three amino acid substitutions were introduced to reduce FcγRI binding. These are the substitutions at EU index positions 234, 235, and 237. Substitutions at these positions have been shown to reduce binding to FcγRI (Duncan et al., 1988). These amino acid substitutions may also reduce FcγRIIa binding, as well as FcγRIII binding (Sondermann et al., 2000; Wines et al., 2000).

Several groups have described the relevance of EU index positions 330 and 331 in complement C1q binding and subsequent complement fixation (Canfield and Morrison, 1991; Tao et al., 1993). Amino acid substitutions at these positions were introduced in Fc4 to reduce complement fixation. The CH3 domain of Fc4 is identical to that found in the corresponding wild-type polypeptide, except for the stop codon, which was changed from TGA to TAA to eliminate a potential dam methylation site when the cloned DNA is grown in dam plus strains of *E. coli*.

In Fc5, the arginine residue at EU index position 218 was mutated back to a lysine, because the BglII cloning scheme was not used in fusion proteins containing this particular Fc. The remainder of the Fc5 sequence matches the above description for Fc4.

Fc6 is identical to Fc5 except that the carboxyl terminal lysine codon has been eliminated. The C-terminal lysine of mature immunoglobulins is often removed from mature immunoglobulins post-translationally prior to secretion from B-cells, or removed during serum circulation. Consequently, the C-terminal lysine residue is typically not found on circulating antibodies. As in Fc4 and Fc5 above, the stop codon in the Fc6 sequence was changed to TAA.

Fc7 is identical to the wild-type γ1 Fc except for an amino acid substitution at EU index position 297 located in the $C_{H2}$ domain. EU index position Asn-297 is a site of N-linked carbohydrate attachment. N-linked carbohydrate introduces a potential source of variability in a recombinantly expressed protein due to potential batch-to-batch variations in the carbohydrate structure. In an attempt to eliminate this potential variability, Asn-297 was mutated to a glutamine residue to prevent the attachment of N-linked carbohydrate at that residue position. The carbohydrate at residue 297 is also involved in Fc binding to the FcRIII (Sondermann et al., Nature 406: 267 (2000)). Therefore, removal of the carbohydrate should decrease binding of recombinant Fc7 containing fusion proteins to the FcγRs in general. As above, the stop codon in the Fc7 sequence was mutated to TAA.

Fc8 is identical to the wild-type immunoglobulin γ1 region shown in SEQ ID NO:4, except that the cysteine residue at EU index position 220 was replaced with a serine residue. This mutation eliminated the cysteine residue that normally disulfide bonds with the immunoglobulin light chain constant region.

The use of any of these specific Fc domains for formation of an TACI-Ig fusion protein is within the scope of the present invention.

The immunoglobulin constant domain of TACI-Ig preferably comprises or consists of a polypeptide having an amino acid sequence of SEQ ID NO: 2, or a variant thereof being at least 80% or 85%, preferably at least 90% or 95% or 99% identical to the Ig constant domain of SEQ ID NO: 2, or a variant comprising less than 50 or 40 or 30 or 20 or 10 or 5 or 3 or 2 conservative amino acid substitutions, as long as there is no impact on the overall biological activity of the TACI-Ig fusion protein, and the immunogenicity of the TACI-Ig protein is not significantly higher that that of atacicept (SEQ ID NO: 3).

In the context of the present invention, the term "identity" reflects a relationship between two or more polypeptide sequences, determined by comparing the sequences. In general, identity refers to an exact amino acid to amino acid correspondence of the two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity of two or more sequences are well known in the art. Thus for instance, programs available in the Wisconsin Sequence Analysis Package, version 9.1 (Devereux J et al., 1984), for example the programs BESTFIT and GAP, may be used to determine the % identity between two polynucleotides and the % identity between two polypeptide sequences. BESTFIT uses the "local homology" algorithm of Smith and Waterman (1981) and finds the best single region of similarity between two sequences. Other programs for determining identity sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990).

Preferred amino acid substitutions in accordance with the present invention are what are known as "conservative" substitutions. Conservative amino acid substitutions of the extracellular domain of TACI or the immunoglobulin constant domain portion of the TACI-Ig fusion protein, include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under 50 or under 30, under 20, or preferably under 10 or under 5 amino acid residues, and do not remove or displace amino acids which are critical to a functional conformation, such as e.g. cysteine residues. Proteins and variants produced by such deletions and/or insertions can be used for treatment of relapsing MS as long as its biological activity is not significantly lower than the biological activity of atacicept (a protein having an amino acid sequence of SEQ ID NO: 3).

International patent applications published as WO 00/40716 and WO 02/094852 disclose sequences for the extracellular domain of TACI as well as specific fragments of the TACI extracellular domain that interact with its ligands, BlyS and APRIL.

As disclosed e.g. in WO 00/40716, the TACI extracellular domain comprises two cysteine (Cys)-rich repeats which are characteristic for members of the tumor necrosis factor (TNF) receptor superfamily, to which the TACI receptor belongs. In WO 00/40716, it has also been established that a splice variant of TACI, designated BR42×2, comprising only the second, less conserved Cys-rich repeat, was able to bind to BlyS. Therefore, in the frame of the present invention, the TACI extracellular domain fragment preferably at least comprises or consists of amino acid residues 71 to 104 of SEQ ID NO: 1, corresponding to the second Cys-rich repeat. It is further preferred that the TACI-Ig fusion protein further comprises amino acid residues 34 to 66 of SEQ ID NO: 1, corresponding to the first Cys-rich repeat.

In a further embodiment of the present invention, said TACI extracellular domain fragment, which binds to and inhibits BlyS and/or APRIL activity, comprises or consists of amino acid residues 30 to 110 of SEQ ID NO: 1.

In yet a further embodiment of the invention, the TACI-Ig fusion protein comprises or consists of a polypeptide having the sequence of SEQ ID NO: 3, or a variant thereof being at least 90% or 95% or 98% or 99% identical thereto or having less than 30 or 20 or 15 or 10 or 5 or 3 or 2 conservative amino acid substitutions, the variant binding to BlyS and/or APRIL.

In yet a further embodiment of the invention, the TACI-Ig fusion protein comprises or consists of a polypeptide having the sequence of SEQ ID NO: 8, or a variant thereof being at least 90% or 95% or 98% or 99% identical thereto or having less than 30 or 20 or 15 or 10 or 5 or 3 or 2 conservative amino acid substitutions, the variant binding to BlyS and/or APRIL.

In yet a further embodiment of the invention, the TACI-Ig fusion protein comprises or consists of a polypeptide having the sequence of SEQ ID NO: 10, or a variant thereof being at least 90% or 95% or 98% or 99% identical thereto or having less than 30 or 20 or 15 or 10 or 5 or 3 or 2 conservative amino acid substitutions, the variant binding to BlyS and/or APRIL.

In yet a further embodiment of the invention, the TACI-Ig fusion protein comprises or consists of a polypeptide having the sequence of SEQ ID NO: 12, or a variant thereof being at least 90% or 95% or 98% or 99% identical thereto or having less than 30 or 20 or 15 or 10 or 5 or 3 or 2 conservative amino acid substitutions, the variant binding to BlyS and/or APRIL.

In yet a further embodiment of the invention, the TACI-Ig fusion protein comprises or consists of a polypeptide having the sequence of SEQ ID NO: 14, or a variant thereof being at least 90% or 95% or 98% or 99% identical thereto or having less than 30 or 20 or 15 or 10 or 5 or 3 or 2 conservative amino acid substitutions, the variant binding to BlyS and/or APRIL.

In another embodiment of the invention, the formulation comprises a TACI-Ig fusion protein in a concentration ranging from 20 mg/mL to 180 mg/mL, e.g. in a concentration of 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 mg/mL.

In a further embodiment of the invention, the formulation is in liquid (e.g. aqueous) form.

In yet a further embodiment, the formulation according is for multi-dose administration. In the context of a multi-dose formulation, it is preferred to include a preservative. As mentioned above, in a preferred embodiment, the formulation comprises benzyl alcohol (e.g. at 0.3%) and benzalkonium chloride (e.g. at 0.001%).

The TACI-Ig fusion protein formulation may be for administration every day or every other day, preferably twice a week or weekly. Preferably, the administration of TACI-Ig is a bolus administration once per week. Alternatively, the formulation can also be for administration every other week or once per month.

The formulation of the present invention can e.g. be for intravenous, subcutaneous, or intramuscular routes. In an embodiment of the invention, the formulation is for subcutaneous administration.

The formulation of the present invention is intended for treatment of disease, preferably for treatment of human disease. Therefore, in an embodiment, the formulation of the invention is prepared as pharmaceutical composition.

The formulation or pharmaceutical composition comprising a TACI-Ig fusion protein is preferably for treatment of, or for the preparation of a medicament for treatment of, an autoimmune disease or a lymphoproliferative disorder.

An autoimmune disease, in the context of the present invention, includes but is not limited to e.g. systemic lupus erythematosus (SLE), lupus nephritis, rheumatoid arthritis, multiple sclerosis or optic neuritis.

A lymphoproliferative disorder is a disease, in which cells of the lymphatic system grow excessively. B-cell malignancies are e.g. lymphoproliferative disorders. B-cell malignancies include but are not limited to leukemias and lymphomas, such as e.g. acute leukemia, acute lymphocytic leukemia, acute myelocytic leukemia, myeloblastic leukemia, promyelocytic leukemia, myelomonocytic leukemia, monocytic erythroleukemia, chronic leukemia, chronic myelocytic (granulocytic) leukemia, chronic lymphocytic leukemia, polycythemia vera, Hodgkin's disease, non-Hodgkin's lymphoma, multiple myeloma, and Waldenstrom's macroglobulinemia.

The present invention also relates to a process for the production or preparation of a formulation according to the invention, comprising the step of preparing (e.g. by admixing) the components of (a) to (c), preferably in a liquid (e.g. aqueous) solution.

The present invention also relates to a process for the production or preparation of a formulation according to the invention, comprising the step of placing a predetermined amount of the formulation into a sterile container. A predetermined amount can e.g. be 0.5 to 5 mL, preferably 1 to 2 mL.

In an embodiment of the invention, the container is selected from a glass vial or a pre-filled syringe. The glass vial can e.g. be closed using an uncoated stopper or a coated stopper. The stopper can e.g. be a rubber stopper or a bromobutyl stopper. The syringe, e.g. a pre-filled syringe, can be stoppered with a rubber plunger or with a coated plunger. The coating can e.g. be a silicone oil-free coating.

A prefilled syringe can have different volumes such as 0.5, 1, 1, 5, or 2 mL. Preferably, it is a 1 mL syringe. The filling volume of the syringe is preferably 1 or 1.2 mL. The prefilled syringe can be made of plastic or, preferably, it can be a glass syringe. An appropriate glass syringe is e.g. the 1 mL Hypac glass syringe 27G1/2 RNG W 7974/50G, manufactured by Becton Dickinson. The prefilled syringe can preferably be stoppered with a coated stopper (e.g. W4023/50G, manufactured by FluoroTec) and an uncoated plunger (e.g. W4023/50G, manufactured by West Pharmaceutical). In accordance with the present invention, the prefilled syringe preferably comprises an amount of a TACI-Ig fusion protein in the range of 20 to 160 mg, such as e.g. 20, 25, 50, 75, 100, 125 or 150 mg of drug substance. As shown in Example 4 below, a formulation of a TACI-Ig fusion protein at pH 5.0, comprising sodium acetate buffer and trehalose, was stable over extended periods of time, e.g. up to 18 months, when kept at 5 or 25° C.

The use of numerical values in the various ranges specified in this application, unless expressly indicated otherwise, are stated as approximations as though the minimum and maximum values within the stated ranges were both preceeded by the word "about." In this manner, slight variations above and below the stated ranges can be used to achieve substantially the same results as values within the ranges. Also, the disclosure of ranges is intended as a continuous range including every value between the minimum and maximum values recited as well as any ranges that can be formable thereby.

In the context of the present invention, the formulation or pharmaceutical composition of the invention can comprise or be administered in combination with further active ingredients in addition to a TACI-Ig fusion protein. For instance, a corticosteroid, in particular methylprednisolone, may be present. Additionally, interferon-beta, cladribine, mitoxantrone, glatiramer acetate, natalizumab, rituximab, teriflunomide, fingolimod, laquinimod, or BG-12 (an oral fumarate). The combined treatment can be simultaneous, separate or sequential.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within a range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Having now described the invention, it will be more readily understood by reference to the following example of an exemplary clinical study outline, that is provided by way of illustration, and not intended to be limiting of the present invention.

EXAMPLE 1

Development of a Liquid Formulation

Glossary

AUC: Analytical UltracentrifugationCD: Circular Dichroism
DLS: Dynamic Light Scattering
DSC: Differential Scanning Calorimetry
IEC: Ionic Exchange Chromatography
MALDI-ToF: Matrix Assisted Laser Desorption Ionization Time-of-Flight mass spectrometry
OD: Optical Density
RALS: Right Angle Light Scattering
RP: Reverse Phase Chromatography
SEC: Size Exclusion Chromatography.
Materials
  TACI-Fc drug substance in phosphate buffer pH 6+140 mM NaCl
  TACI-Fc drug substance in phosphate buffer pH 5
  TACI-Fc drug substance in acetate buffer pH 5
  ortho-Phosphoric acid (1.00563, Merck)
  Succinic acid (1.00682, Merck)
  Citric acid (1.59134, Merck)
  Histidine (1.04351, Merck)
  Glacial acetic acid 100% (1.00063, Merck);
  D-Mannitol DAB, Ph Eur, BP, USP, FCC, E421 (1.05980, Merck)
  D-Sorbitol (S-1876, Sigma)
  Sucrose DAB, Ph Eur, BP, NF (1.07653, Merck)
  Trehalose (1.08216, Merck)
  D-Glucose monohydrate (346971, Carlo Erba)
  Sodium hydroxide pellets GR (1.06498, Merck)
  Tween 20 for synthesis (8.22184, Merck);
  Poloxamer 188 (Lutrol F 68 DAC, USP/NF, Basf)
  Calcium chloride dihydrate (1.02382, Merck)
  Magnesium chloride (1.05833, Merck)
  Sodium chloride (1.06404, Merck)
  Arginine hydrochloride (A-5131, Sigma);
  Lysine hydrochloride (1.0571, Merck)
  Glycine (5.00190, Merck);
  Acetonitrile (00030, Merck)
  10×PBS (P/N 70013-032, Gibco)
  Trifluoroacetic acid (9470, Baker)
  Ammonium sulfate (1.01217, Merck)
  1N Sodium hydroxide (1.09137, Merck)
  1N Hydrochloric acid (1.09057, Merck)
  HPLC grade water (MilliQ)
  Water for Injection
  Sodium sulfate anhydrous (code 6649, Merck)
  Methanol (code 06009, Merck)
  Sodium azide (code 6688, Merck)
  Sodium di-hydrogen phosphate monohydrate (code 06346, Merck)
  Disodium hydrogen phosphate dihydrate (code 06580, Merck)
For Bioassay:
  Jurkat pKZ142 clone 24 cells (WCB)
  TACI-Fc5 (1-8.66 mg/mL)
  zTNF4 (1.44 mg/mL)
  RPMI 1640 with and without phenol red (Gibco)
  Foetal Bovine Serum (FBS) (GIBCO)
  L-glutamine (Hyclone)
  Sodium Pyruvate (Gibco) Puromycin (Sigma)
  Steady GLO Luciferase Assay Buffer and Substrate (ProMega E2510)
White tissue culture 96 well plates with lids (Dynex)
  96 wells plates with covers (Falcon)
  5 mL polypropylene tubes (Falcon)
Equipment
  HPLC systems (Waters)
  Calibrated pipettes (Gilson)
  Differential Scanning Calorimeter (mod. 2920, TA Instruments)
  Microcalorimeter (mod. VP-DSC, MicroCal)
  pH meters (mod. 713, Metrohm)
  Osmometer (Osmomat 030-D, Gonotec)
  Spectopolarimeter J-810 equipped with a Peltier control for temperature, PTC-4235 (Jasco)
  Spectrofluorometer FluoroMax3 equipped with a microplate reader, MicroMax384 (Jobin Yvon)
  96-well MaxSorp plates (Nunc)
  Spectrophotometer lambda 354 (Perkin-Elmer)
  Quartz cuvettes 0.1 and 1 cm pathlength (Perkin Elmer)
  Zetasizer Nano Series (Malvern)
  Reduced volume (~70 µL) quartz cuvettes
  Stirred Cell system (mod. 8400 or 8450, Amicon)
  10 kDa cut-off membrane (type YM10, Amicon)
Stainless steel holders 22 mL and 220 mL capacity (Sartorius)
  Membrane filters 0.22 µm (Durapore type GWVP, Millipore)
  Membrane filters 0.45 µm (Durapore type HVLP, Millipore)
  Fluorescence/RALS spectrometer (Photon Technology International)
  IKA-Vibrax-VXR shaker (IKA-Works, Inc.)
  Freeze-dryers (Lyoflex 06, Lyoflex 08, Edwards)
  Vortex (Falc)
  Thermostatic cabinets (Heraeus)
  Freezers (Angelantoni)
For Bioassay:
  Luminometer plate reader, Lumicount Packard
  Graph Pad Prism Software
  Laminar Flow Hood (Flow Laboratories)
  Incubator 37° C. and CO2 (Heraeus)
  Water bath 37° C.
  Cell Coulter
  Microscope
  Shaking Platform
  Table top Centrifuge
  Calibrated single and multi-channel pipettes and pipette tips
  Pipette aid
Primary Packaging Material
  DIN2R (3 mL) glass vials (Nuova OMPI)
  Fluorotec rubber stoppers (S2F452, D777-1, B2-40, West Pharmaceutical)
  Rubber stoppers (1779 W1816 grey, Pharmagummi)
Methods
Size Exclusion Chomatography (SEC)
Method 1

The samples were diluted to 0.5 mg/mL with PBS1× pH=7.2 and 40 µL (20 µg) loaded onto a TSK gel G3000SWXL 5 µm, 7.8×300 mm. For every run, the eluent was 0.05 M sodium phosphate, 0.5 M ammonium sulphate, pH=6.0.

Method 2

The samples were diluted to 0.25 mg/mL in the mobile phase and 40 µL (20 µg) loaded onto a TSK gel G3000SWXL 5 µm, 7.8×300 mm connected to a TSK gel SWXL guardcolumn 6 mm×4 cm. For every run, the eluent was 0.05 M sodium phosphate, 0.5 M ammonium sulphate, pH=6.0.

Reverse Phase Chromatography (RP)

The samples were diluted to 0.5 mg/mL with PBS1× pH=7.2 and 40 µL (20 µg) loaded onto a PLRP 4000 Å column 8 µm, 50×4.6 mm equilibrated in 71% buffer A (0.1% TFA in water) and 29% buffer B (0.1% TFA in acetonitrile). The samples were eluted using a linear gradient with a flow rate of 2 mL/min. The calibration curve was generated by injecting different amounts of standard (IRS TACI-Fc5 2002/2001).

C-Terminus Truncation (RP)

Samples were submitted to enzymatic digestion (Lys-C) for 2 hours at 37° C. and then run onto Reverse phase chromatography on Vydac C18 (4.6×50 mm) with guard column,
Eluent A: 0.1% TFA in water
B: 0.08% TFA in CH3CN 70%
Flow: 1 mL/min
T.: 40°+/−5° C.
Detection: 214 nm
Elution gradient: from 15% B to 23% in 7 minutes. Total 15 minutes.

Clipped Forms (RP)

TACI-Fc drug product samples were diluted in purified water in order to obtain a protein concentration of 4 mg/mL. Then, 10 µL of the diluted sample are diluted in 200 µL of the denaturising-reducing solution (0.15 M DTT in guanidine 6M), vortexed and finally incubated at 60±2° C. for 90 minutes. 75-150 µL (15-30 µg) are injected in the column (widepore butyl, 5 mm, 4.6 mm i.d.×50 mm, cod. 7116-05 by J. T. Baker) previously equilibrated with the starting conditions (71% eluent A, 0.05% trifluoroacetic acid in water and 29% eluent B, 0.04% trifluoroacetic acid in acetonitrile).

Free-Fc Dimer (IEC)

TACI-Fc drug product samples were diluted in a solution of Poloxamer 188 100 mg/L in 10 mM sodium phosphate buffer pH 4.00 in order to obtain a protein concentration of 10 mg/mL. In case of concentration of TACI-Fc higher than 100 mg/mL, the dilution of samples should be performed by weighing.

25 µL (250 µg) are injected in the column (ProPac WCX-10G (guard), 4×50 mm, cod. 054994 by Dionex) previously equilibrated with the starting conditions (80% eluent A, 10 mM Sodium Phosphate pH 4.00 and 20% eluent B, 10 mM Sodium Phosphate pH 4.00+0.5M KCl).

Oxidized Forms (MALDI-ToF)

A peptide mapping was developed on TACI-Fc drug substance samples and the applicability of MALDI-ToF detection for quantification of the oxidised forms verified.

Analytical Ultracentrifugation (AUC)

The samples were loaded into cells with 2-channel charcoal-epon centrepieces with 12 mm optical pathlength. Samples were diluted using SE-HPLC elution buffer as diluent so as to mimic the conditions of the HPLC testing. The corresponding buffer was loaded in the reference channel (the instrument works like a dual-beam spectrophotometer). The loaded cells were then placed into an AN-50Ti analytical rotor, loaded into a Beckman Optima XL-I analytical centrifuge. The analysis was carried out with the following experimental settings:

Rotor type: 8-holes rotor
Rotor speed: 40K rpm
Centrepieces: charcoal-epon
Channel length: 12 mm
Temperature during the AUC run: 20° C.±0.2° C.
Detection wavelength: 280 nm
Sample concentration: 0.5 mg/mL
Sample volume: 432 mL/channel
Reference volume: 442 mL/channel The data were analysed using the c(s) method developed by Peter Schuck at the N.I.H. and implemented in his analysis program SEDFIT (version 8.7).

Differential Scanning Calorimetry (DSC)

DSC 2920 CE by TA Instrument: T range=25-100° C.; heating rate=2° C./min; high volume pans (HVP) were filled with 75 µL of solution; placebos were used as reference solutions. Microcalorimeter MicroCal VP-DSC: T range=25-100° C.; heating rate=70° C./hour; response=15 s; data pitch=0.2-8° C.; the sample cell was filled with about 600 mL of 5 mg/mL Taci-Fc5 solution; water was used as reference solution.

Optical Density (OD)

0.5 mg/mL TACI-Fc5 solutions were prepared (by dilution with water) and their concentrations (c) obtained by the Lambert-Beer equation: OD=εbc (ε=molar extinction coefficient; b=optical cell thickness). ε (280 nm)=1.56 (mL/mg)·cm$^{-1}$. The concentration of the starting solutions was determined by multiplying these calculated values by dilution factor.

Circular Dichroism (CD)

Conformational Analysis

CD is commonly used for studying peptide and protein conformation. Several factors can affect the appearance of the characteristic peaks in CD spectra, both in the far UV (180-250 nm) and in the near UV region (250-350 nm), such as protein concentration, temperature, pH and ionic strength. General band positions observed in the far UV are reported in literature and represent particular types of secondary structure (α-helix, β-sheet, random coil). The CD bands observed in the near UV range are mainly due to the Trp, Tyr, Phe and disulfide bonds.

However it must be pointed out that the signal from the disulfide bond is generally much weaker than those of the aromatic amino acids. As long as these residues lay in an asymmetric environment a CD signal can be provided. Conformational changes in the protein's tertiary structure usually lead to variations of the starting environment thus causing a modification in the CD spectrum. In fact, in a native protein individual amino acids occupy unique positions within the three-dimensional structure. Alterations in this structure could lead to a change in their accessibility.

Near UV CD Spectra Settings

Scan rate=5-20 nm/min; range=250-350 nm; response=8 s; concentration=2 mg/mL; pathlength=1 cm; data pitch=0.5 nm; bandwidth=1 nm; accumulations=2. Standard sensitivity. The spectra were acquired at room temperature.

Far UV CD Spectra Settings

Scan rate=5-20 nm/min; range=200-300 nm; response=8s; concentration=0.25 mg/mL; path length=0.1 cm; data pitch=0.5 nm; bandwidth=1 nm; accumulations=2. Standard sensitivity. The spectra were acquired at room temperature.

Unfolding Temperatures

Temperature scans monitored by CD at a fixed wavelength are a valuable tool to investigate into both secondary and tertiary structure of the protein at different temperatures. Such measurement makes it possible to evaluate the protein unfolding temperature ($T_{unf}$) in different formulations. Although $T_{unf}$ doesn't have a straightforward relationship with the free energy of protein unfolding (which is an indicator of protein stability), it is widely accepted that any increase in $T_{unf}$ should be correlated with an increase in protein stability. Therefore, a change in Tm might indicate if a particular composition has any stabilizing or destabilizing effect. Thermal denaturation was investigated by monitoring the Trp (tryptophan)'s signal variation associated with protein conformational change with temperature. The drug substance formulations underwent a heating (1° C./min) in the range 55-70° C. The effect of temperature on tertiary structure was detected by changes in the CD ellipticity relative minimum at 292.5 nm. Fourth grade polynomial fits were used to calculate the values of transition temperatures.

CD Temperature Scan Settings

T range=55-70° C.; heating rate=1° C./min; A=292.5 nm; concentration=2 mg/mL; response=8 s; data pitch=0.2-8° C.; bandwidth=1.5 nm. Standard sensitivity. Stirring rate=low.

Dynamic Light Scattering (DLS)

Dynamic light scattering measures scattering induced by Brownian motion of particles and relates it to the size of the particles. It requires submitting the particles to a laser beam and analyzing the intensity fluctuations in the scattered light. More precisely, the speed of the particles that move due to Brownian motion is related to the size of the particles (Stokes-Einstein equation). The digital correlator measures the degree of similarity between two signals (intensity signals in this case) over a period of time and it gives information related to the nature and extent of the scattering intensity fluctuations, which are related to the dimensions of the particles. After the correlation function has been determined, it can then be used to calculate the size distribution.

The Zetasizer Nano Series measures the scattering intensity close to 180° (backscatter detection). Such configuration reduces the effect of multiple scattering through the sample and the effect of large contaminants. The disposable sizing cuvette (internal volume ~70 µL) was used. The measurements were carried out at T=25° C. Equilibration time=1 min; number of runs=11; run duration=10 s; number of measurements=2. Dispersant: water (viscosity=0.8872 cP; refractive index=1.330). No dilutions were made.

Right Angle Light Scattering (RALS) Using Fluorescence

RALS is measured using a fluorescence detector in which the excitation and emission wavelengths have been set identically. In this configuration, the fluorescence detector becomes a very sensitive RALS detector. Increases in RALS are indicative of aggregation/precipitation in a sample.

Fluorescence

Intrinsic Fluorescence

Proteins contain three aromatic amino acid residues (tryptophan: Trp; tyrosine: Tyr; phenylalanine: Phe), which may contribute to their intrinsic fluorescence. The fluorescence of a folded protein is a combination of the fluorescence from individual aromatic residues. Protein fluorescence is generally excited at 280 nm or at longer wavelengths, usually at 295 nm. Most of the emissions are due to excitation of tryptophan residues, with a few emissions due to tyrosine and phenylalanine. The intensity, quantum yield and wavelength of maximum fluorescence emission of tryptophane is very solvent dependent. The fluorescence spectrum shifts to shorter wavelength and the intensity of the fluorescence increases as the polarity of the solvent surrounding the tryptophane residues decreases. Tryptophan residues, which are buried in the hydrophobic core of proteins, can have spectra which are shifted by 10 to 20 nm compared to tryptophans on the surface of the protein. Moreover tryptophan fluorescence can be quenched by neighbouring protonated acidic groups such as Asp or Glu. Thus fluorescence can be used as a powerful monitoring tool, which reflects the variations in the microenvironment in which the aromatic residues lay.

The MicroMax 384 is a microwell-plate reader able to accept plates with up to 384 wells and connect to the FluoroMax spectrofluorometer. Light from the excitation and emission monochromators is carried via a fiber-optic bundle to and from the MicroMax 384, thus the user may scan with the main spectrofluorometer and select any excitation and emission wavelength pair for intensity measurements. All control of the MicroMax 384 is automated through DataMax software; custom selection of Microwells on the plate is possible through the software.

The high throughput fluorescence scans were run using the Micromax 384 plate reader using the following settings: excitation and emission slits=5 nm; λexc=280 nm; emission range=300-450 nm; integration time=0.1 s. No dilution was made. The maximum emission wavelength was automatically calculated by the Fluoromax 3 software.

RALS

Measurements of RALS are performed by running synchronous scans (λexc=λem) with the FluoroMax spectrofluorimeter between 500-800 nm. Under these conditions (no absorption by sample and no influence by light source) the revealed intensity is mainly due to scattering phenomena (incident light/protein) occurring in solution. The total scattered intensity increases with increasing protein dimensions, thus this technique can be useful to monitor the occurrence of events such as aggregation, subunit dissociation, degradations, etc.

Scattering intensity also depends on protein concentration and refractive index, so comparative measurements should be performed at the same protein concentration.

RALS measurements were carried out by setting the following parameters: synchronous scan; wavelength range=500-800 nm; slits=15 nm; integration time=0.5 s; offset=0 nm; sample concentration=35 mg/mL (milliQ water was used as diluent).

Anisotropy of Fluorescence Emission

The rotation of macromolecules depends on their size, shape and local environment (i.e. solvent). Polarized emission measurements are often used to detect small changes in molecular size (aggregation, binding, cleavage) as well as environmental changes (local viscosity, phase transitions, etc). The first step in these measurements is the excitation of a selected group of fluorophores (photoselection). Vertically polarized light is typically used to excite a population of molecules whose absorption dipole is oriented in the vertical direction. In this phase, vertically polarized exciting light is produced using a polarizer in the excitation path. Once excited, the molecule may rotate during the lifetime of the excited state (~$10^{-9}$ s). Such rotation will depolarize the fluorescence emission. Measurements of the polarized emission components allows calculation of the type and extent of rotational motions of the molecule. The polarized components of fluorescence emission are measured using a polarizer in the emission path. From the magnitude of the vertical (V) and horizontal (H) emission components, the extent and type of rotational behaviour can be calculated. Anisotropy (A) is a ratio defined as the difference between the linearly polarized component's intensity divided by the total light intensity:

$$A=(I_{VV}-G*I_{VH})/(I_{VV}+2G*I_{VH})$$

Where:

G is a correction factor, $G=I_{HV}/I_{HH}$

In these equations, the first subscript for intensity I indicates the position of the excitation polarizer (H or V) and the second the emission polarizer (H or V). Fluorescence anisotropy, when excitation wavelength is set at λ=295 nm, gives information related to the mobility of Trp's residues and on the local viscosity that they experience. Thus, an increase in fluorescence anisotropy can reflect a more rigid environment of these residues in proteins.

Anisotropy measurements were carried out by setting the following parameters: λexc=295 nm; emission range=330-350 nm; integration time=0.5 s; slits=15 nm; sample concentration=35 mg/mL (milliQ water was used as diluent).

Bioassay

The TACI-Fc in vitro bioassay is based on Jurkat (human acute T cell lymphocyte) transfected cells (Jurkat pKZ142). This cell line has been transfected with 2 plasmids. The first one encodes the full length TACI cDNA under control of the CMV promoter and the second one with NF-kB/AP-1 driving a luciferase reporter gene. The method is based on the ability of the zTNF4 to bind the cell surface TACI receptor, triggering a signal transduction cascade, resulting in stimulation of the transfected NF-kB/AP-1 luciferase reporter gene. The presence of soluble TACI-Fc inhibits zTNF4 from binding to TACI receptor, thereby reducing the luciferase expression.

The Jurkat pKZ142 cells were incubated with TACI-Fc standard to build a whole dose-response curve (from 27.86 to 1.63 U/mL) and with samples tested at two concentrations located in the linear part of the standard curve (i.e. 4 and 6 U/mL).

The zTNF4 solution is then added either to standard curve and samples at concentration that is able to induce the submaximal production of luciferase (i.e. 150 ng/mL/well); minimum and maximum luciferase production is also performed as control. After 4 h of incubation at 37° C. (5% $CO_2$), cells are added with luciferase Steady Glo kit and the luciferase expression is detected by a luminometer.

The potency of samples is calculated by interpolating the Y values (RLU) for the two tested concentrations on the linear part of the standard dose-response curve, thus achieving the concentration of TACI-Fc on the x axis (Graph Pad software). The values of the two concentrations of independent assays are averaged and then the TACI-Fc5 biological activity is calculated performing the arithmetic mean of the potency obtained from each independent assay.

Pre-Formulation Process

The effect of pH, buffer type and excipients on the protein stability was evaluated.

Solutions of TACI-Fc at a concentration of 70 or 100 mg/mL were prepared to preliminary investigate the following variables:

pH (4, 5, 6, 7)
buffer (acetate, phosphate, succinate, citrate, histidine)
sugars (mannitol, sorbitol, glucose, sucrose, trehalose)
excipients (sodium chloride, magnesium chloride, calcium chloride, glycine)

In addition to this, the following further prescreening studies were carried out on TACI-Fc5 at 70 mg/mL:
freeze-thaw (F-T) cycles (1, 3, 5 F-T) in 20 mM buffer (histidine, phosphate, succinate, citrate) at pH 5-6-7;
incubation at 40° C. (shaking & non-shaking conditions);
storage at 2-8° C. in 20 mM buffer (acetate, histidine, phosphate) at pH 4-5-6.

Based on the results arising from these first observations, two buffers (phosphate and histidine) at pH 5 and 6 were selected and a second set of formulations prepared to investigate the effect of the inclusion of additional stabilizing agents (at 0.280 OSM of residual osmolality). The following stabilizing agents were tested: Glucose, Mannitol, Sorbitol, Sucrose, Trehalose, Glycine, NaCl, $MgCl_2$, $CaCl_2$.

The solutions were stored at 2-8° C., 25° C. and 40° C. and tested up to 14 days for aggregates (SE-HPLC), protein content (RP-HPLC), pH and appearance.

EXPERIMENTAL DESIGN

Based on the selection made during the previous phase, an experimental design was set up to assess the influence of factors previously investigated at different levels with regard to protein stability. Formulations in acetate and histidine buffer were tested together with the following surfactants: Poloxamer 188 (Lutrol® F-68) and Tween 20 and with the following excipients: Arginine, Glycine, Lysine, Mannitol and Trehalose. These formulations were stored in glass vials at 2-8° C., 25° and 40° C. and tested for aggregates (by SE-HPLC and AUC), pH, appearance and osmolality. Biophysical analytical methods (e.g. circular dichroism, $2^{nd}$ UV derivative spectroscopy, intrinsic fluorescence) were also applied.

Candidate Formulations

At the end of the pre-formulation phase, some candidate formulations were identified containing either 70 or 100 mg/mL TACI-Fc, 10 mM acetate buffer, mannitol (51 mg/mL) or trehalose anhydrous (80 or 96 mg/mL) as excipient, either with our without Poloxamer 188 (Lutrol® F-68) (0.05 mg/mL). pH values from 4.8, 5.0, 5.2 and 5.4 were tested.

All the solutions were aseptically filtered through a 0.22 μm Durapore membrane and collected into a sterilized container. The solutions were then filled into DIN2R glass vials (1 mL filling volume). In-process samples (before and after filtration) were taken during manufacturing to assess protein loss or increase in aggregation.

Samples were stored at 2-8° C., 25° C. and 40° C. and tested up to 1 month (40° C.) and 6 months (2-8° C. and 25° C.).

The candidate formulations were tested for aggregates (SE-HPLC, AUC), protein content (SE-HPLC), pH, osmolality and biological activity. The extent of the C-terminus truncation and the percentage of truncated/clipped forms was also determined. Biophysical methods (intrinsic fluorescence, dynamic light scattering, 90° light scattering) have also been applied.

Effect of freeze-thawing was also assessed on liquid samples of the candidate formulations stored at 2-8° C.: the samples were frozen at −80° C. and then thawed at room temperature. The amount of aggregates before and after freezing-thawing was assessed by SE-HPLC.

The effect of 24 hour shaking to simulate the shipment of the drug product was evaluated on samples stored at 2-8° C., which have been placed under shaking on a microplate shaker at room temperature for 24 h. The level of aggregates was assessed by SE-HPLC vs the initial level.

Results

The candidate formulations were in 10 mM Na-Acetate.

| Formulation # | TACI-Fc (mg/mL) | Composition |
| --- | --- | --- |
| 21A | 70 | pH 5, 96 mg/mL Trehalose, 0.05 mg/mL Poloxamer 188 (Lutrol ® F-68) |
| 21B | 70 | pH 5, 80 mg/mL Trehalose |
| 21C | 70 | pH 5.4, 80 mg/mL Trehalose, 0.05 mg/mL Poloxamer 188 (Lutrol ® F-68) |

-continued

| Formulation # | TACI-Fc (mg/mL) | Composition |
|---|---|---|
| 21D | 100 | pH 5, 80 mg/mL Trehalose, 0.05 mg/mL Poloxamer 188 (Lutrol ® F-68) |
| 21E | 100 | pH 5, 80 mg/mL Trehalose |
| 21F | 100 | pH 5.4, 80 mg/mL Trehalose, 0.05 mg/mL Poloxamer 188 (Lutrol ® F-68) |
| 21G | 100 | pH 5, 51 mg/mL Mannitol, 0.05 mg/mL Poloxamer 188 (Lutrol ® F-68) |
| 21H | 100 | pH 5, 51 mg/mL Mannitol |
| 21I | 100 | pH 4.8, 80 mg/mL Trehalose, 0.05 mg/mL Poloxamer 188 (Lutrol ® F-68) |
| 21L | 100 | pH 5.2, 80 mg/mL Trehalose, 0.05 mg/mL Poloxamer 188 (Lutrol ® F-68) |

The detailed results are reported in the following tables A to T.

TABLE A

Total aggregates % by SE-HPLC (2-8° C.)

| Formulation | TACI-Fc5 (mg/mL) | Composition | time 0 | 4 w | 6 w | 8 w | 12 w | 16 w | 26 w |
|---|---|---|---|---|---|---|---|---|---|
| 21A | 70 | pH 5, 96 mg/mL Tre, F68 0.05 | 3.3 | 3.6 | 3.7 | 3.2 | 2.9 | — | 2.0 |
| 21B | 70 | pH 5, 80 mg/mL Tre | 3.4 | 3.7 | 3.8 | 3.5 | 3.0 | — | 2.1 |
| 21C | 70 | pH 5.4, 80 mg/mL Tre, F68 0.05 | 3.4 | 3.6 | 3.8 | 3.9 | 3.1 | — | 2.2 |
| 21D | 100 | pH 5, 80 mg/mL Tre, F68 0.05 | 3.4 | 3.6 | 3.9 | 3.5 | 3.0 | — | 2.3 |
| 21E | 100 | pH 5, 80 mg/mL Tre | 3.7 | 4.5 | 3.8 | 3.8 | 3.3 | — | 2.3 |
| 21F | 100 | pH 5.4, 80 mg/mL Tre, F68 0.05 | 3.6 | 3.7 | 3.9 | 3.4 | 3.4 | — | 2.8 |
| 21G | 100 | pH 5, 51 mg/mL Man, F68 0.05 | 3.7 | 3.7 | 3.9 | 4.1 | 3.2 | — | 2.6 |
| 21H | 100 | pH 5, 51 mg/mL Man | 3.8 | 3.7 | 4.1 | 3.6 | 3.3 | — | 2.6 |
| 21I | 100 | pH 4.8, 80 mg/mL Tre, F68 0.05 | 3.6 | 3.3 | 2.9 | 3.0 | — | 2.6 | — |
| 21L | 100 | pH 5.2, 80 mg/mL Tre, F68 0.05 | 3.6 | 3.4 | 3.3 | 3.3 | — | 2.7 | — |

Bulk used: S128/L20a (10 mM sodium acetate buffer, pH = 5.0).
Total aggregates % = 3.9

TABLE B

Total aggregates % by SE-HPLC (25° C.)

| Formulation | TACI-Fc5 (mg/mL) | Composition | time 0 | 2 w | 4 w | 6 w | 8 w | 12 w | 17 w | 27 w |
|---|---|---|---|---|---|---|---|---|---|---|
| 21A | 70 | pH 5, 96 mg/mL Tre, F68 0.05 | 3.3 | 2.6 | 4.0 | 3.8 | 3.7 | 3.5 | — | 3.4 |
| 21B | 70 | pH 5, 80 mg/mL Tre | 3.4 | 3.0 | 3.7 | 4.1 | 3.9 | 3.4 | — | 3.5 |
| 21C | 70 | pH 5.4, 80 mg/mL Tre, F68 0.05 | 3.4 | 3.1 | 3.9 | 4.2 | 4.6 | 4.0 | — | 4.5 |
| 21D | 100 | pH 5, 80 mg/mL Tre, F68 0.05 | 3.4 | 5.0 | 4.0 | 4.1 | 4.4 | 4.2 | — | 4.4 |
| 21E | 100 | pH 5, 80 mg/mL Tre | 3.7 | 3.3 | 3.9 | 4.6 | 4.5 | 4.4 | — | 4.7 |
| 21F | 100 | pH 5.4, 80 mg/mL Tre, F68 0.05 | 3.6 | 3.8 | 4.5 | 5.0 | 5.1 | 5.2 | — | 6.5 |
| 21G | 100 | pH 5, 51 mg/mL Man, F68 0.05 | 3.7 | 3.9 | 3.9 | 4.7 | 4.7 | 4.5 | — | 4.9 |
| 21H | 100 | pH 5, 51 mg/mL Man | 3.8 | 3.4 | 3.9 | 4.6 | 4.5 | 4.4 | — | 4.9 |
| 21I | 100 | pH 4.8, 80 mg/mL Tre, F68 0.05 | 3.6 | 3.0 | 3.6 | 3.3 | 3.5 | — | 5.0 | — |
| 21L | 100 | pH 5.2, 80 mg/mL Tre, F68 0.05 | 3.6 | 3.4 | 4.1 | 3.8 | 4.2 | — | 4.9 | — |

Bulk used: S128/L20a (10 mM sodium acetate buffer, pH = 5.0).
Total aggregates % = 3.9

TABLE C

Total aggregates % by SE-HPLC (40° C.)

| | TACI-Fc5 (mg/mL) | Composition | time 0 | 1 w | 2 w | 4 w |
|---|---|---|---|---|---|---|
| 21A | 70 | pH 5, 96 mg/mL Tre, F68 0.05 | 3.3 | 3.9 | 4.1 | 6.1 |
| 21B | 70 | pH 5, 80 mg/mL Tre | 3.4 | 4.0 | 4.4 | 6.3 |
| 21C | 70 | pH 5.4, 80 mg/mL Tre, F68 0.05 | 3.4 | 4.4 | 5.3 | 7.4 |
| 21D | 100 | pH 5, 80 mg/mL Tre, F68 0.05 | 3.4 | 5.0 | 5.3 | 7.9 |
| 21E | 100 | pH 5, 80 mg/mL Tre | 3.7 | 5.0 | 5.5 | 7.9 |
| 21F | 100 | pH 5.4, 80 mg/mL Tre, F68 0.05 | 3.6 | 6.2 | 7.4 | 11.0 |
| 21G | 100 | pH 5, 51 mg/mL Man, F68 0.05 | 3.7 | 5.0 | 6.1 | 8.4 |
| 21H | 100 | pH 5, 51 mg/mL Man | 3.8 | 5.9 | 6.1 | 8.4 |
| 21I | 100 | pH 4.8, 80 mg/mL Tre, F68 0.05 | 3.6 | 6.1 | 7.4 | 12.2 |
| 21L | 100 | pH 5.2, 80 mg/mL Tre, F68 0.05 | 3.6 | 7.6 | 8.9 | 14.0 |

Bulk used: S128/L20a (10 mM sodium acetate buffer, pH = 5.0).
Total aggregates % = 3.9

TABLE D

% Dimer by AUC (2-8° C.)

| | TACI-Fc5 (mg/mL) | Composition | 4 w | 8 w | 13 w |
|---|---|---|---|---|---|
| 21A | 70 | pH 5, 96 mg/mL Tre, F68 0.05 | 4.0 | 7.4 | 3.0 |
| 21B | 70 | pH 5, 80 mg/mL Tre | 3.2 | 1.6 | 3.6 |
| 21C | 70 | pH 5.4, 80 mg/mL Tre, F68 0.05 | — | 7.5 | 2.6 |
| 21D | 100 | pH 5, 80 mg/mL Tre, F68 0.05 | — | 4.2 | 3.7 |
| 21E | 100 | pH 5, 80 mg/mL Tre | 3.3 | 4.5 | 3.2 |
| 21F | 100 | pH 5.4, 80 mg/mL Tre, F68 0.05 | 4.0 | 2.9 | 4.1 |
| 21G | 100 | pH 5, 51 mg/mL Man, F68 0.05 | 3.1 | 4.0 | 3.1 |
| 21H | 100 | pH 5, 51 mg/mL Man | 3.7 | 4.7 | 2.8 |
| 21I | 100 | pH 4.8, 80 mg/mL Tre, F68 0.05 | 3.9 | — | — |
| 21L | 100 | pH 5.2, 80 mg/mL Tre, F68 0.05 | 3.5 | — | — |

TABLE E

% Large aggregates by AUC (2-8° C.)

| | TACI-Fc5 (mg/mL) | Composition | 4 w | 8 w | 13 w |
|---|---|---|---|---|---|
| 21A | 70 | pH 5, 96 mg/mL Tre, F68 0.05 | 2.3 | 2.8 | 1.1 |
| 21B | 70 | pH 5, 80 mg/mL Tre | 2.0 | 0.5 | 2.5 |
| 21C | 70 | pH 5.4, 80 mg/mL Tre, F68 0.05 | — | 3.0 | 0.6 |
| 21D | 100 | pH 5, 80 mg/mL Tre, F68 0.05 | — | 2.1 | 1.4 |
| 21E | 100 | pH 5, 80 mg/mL Tre | 1.2 | 1.5 | 1.2 |
| 21F | 100 | pH 5.4, 80 mg/mL Tre, F68 0.05 | 1.1 | 0.8 | 1.6 |
| 21G | 100 | pH 5, 51 mg/mL Man, F68 0.05 | 1.5 | 2.1 | 1.5 |
| 21H | 100 | pH 5, 51 mg/mL Man | 1.9 | 2.1 | 1.3 |
| 21I | 100 | pH 4.8, 80 mg/mL Tre, F68 0.05 | 1.9 | — | — |
| 21L | 100 | pH 5.2, 80 mg/mL Tre, F68 0.05 | 2.0 | — | — |

TABLE F

% Dimer by AUC (25° C.)

| | TACI-Fc5 (mg/mL) | Composition | T = 0 (4 w 5° C.) | 4 w | 8 w | 13 w |
|---|---|---|---|---|---|---|
| 21A | 70 | pH 5, 96 mg/mL Tre, F68 0.05 | 4.0 | 2.6 | 3.8 | 5.3 |
| 21B | 70 | pH 5, 80 mg/mL Tre | 3.2 | 3.9 | 3.4 | 2.7 |
| 21C | 70 | pH 5.4, 80 mg/mL Tre, F68 0.05 | — | 2.8 | 4.0 | 5.6 |
| 21D | 100 | pH 5, 80 mg/mL Tre, F68 0.05 | — | 2.4 | 4.2 | 3.2 |
| 21E | 100 | pH 5, 80 mg/mL Tre | 3.3 | 3.3 | 3.7 | 3.7 |
| 21F | 100 | pH 5.4, 80 mg/mL Tre, F68 0.05 | 4.0 | 4.3 | 5.2 | 4.2 |
| 21G | 100 | pH 5, 51 mg/mL Man, F68 0.05 | 3.1 | 3.9 | 3.9 | 3.8 |
| 21H | 100 | pH 5, 51 mg/mL Man | 3.7 | 3.0 | 4.3 | 6.6 |
| 21I | 100 | pH 4.8, 80 mg/mL Tre, F68 0.05 | 3.9 | — | — | — |
| 21L | 100 | pH 5.2, 80 mg/mL Tre, F68 0.05 | 3.5 | — | — | — |

TABLE G

% Large aggregates by AUC (25° C.)

| | TACI-Fc5 (mg/mL) | Composition | T = 0 (4 w 5° C.) | 4 w | 8 w | 13 w |
|---|---|---|---|---|---|---|
| 21A | 70 | pH 5, 96 mg/mL Tre, F68 0.05 | 2.3 | 0.3 | 0.8 | 2.5 |
| 21B | 70 | pH 5, 80 mg/mL Tre | 2.0 | 1.1 | 0.6 | 0.2 |
| 21C | 70 | pH 5.4, 80 mg/mL Tre, F68 0.05 | — | 0.1 | 0.8 | 1.3 |
| 21D | 100 | pH 5, 80 mg/mL Tre, F68 0.05 | — | 0.4 | 1.3 | 0.2 |
| 21E | 100 | pH 5, 80 mg/mL Tre | 1.2 | 0.9 | 0.9 | 0.9 |
| 21F | 100 | pH 5.4, 80 mg/mL Tre, F68 0.05 | 1.1 | 1.6 | 1.2 | 0.7 |
| 21G | 100 | pH 5, 51 mg/mL Man, F68 0.05 | 1.5 | 1.9 | 1.1 | 1.1 |
| 21H | 100 | pH 5, 51 mg/mL Man | 1.9 | 1.5 | 2.6 | 3.6 |
| 21I | 100 | pH 4.8, 80 mg/mL Tre, F68 0.05 | 1.9 | — | — | — |
| 21L | 100 | pH 5.2, 80 mg/mL Tre, F68 0.05 | 2.0 | — | — | — |

TABLE H

% Dimer by AUC (40° C.)

| | TACI-Fc5 (mg/mL) | Composition | T = 0 (4 w 5° C.) | 2 w | 3 w |
|---|---|---|---|---|---|
| 21A | 70 | pH 5, 96 mg/mL Tre, F68 0.05 | 4.0 | — | 4.4 |
| 21B | 70 | pH 5, 80 mg/mL Tre | 3.2 | — | 3.9 |
| 21C | 70 | pH 5.4, 80 mg/mL Tre, F68 0.05 | — | — | 5.3 |
| 21D | 100 | pH 5, 80 mg/mL Tre, F68 0.05 | — | — | — |
| 21E | 100 | pH 5, 80 mg/mL Tre | 3.3 | — | 6.4 |
| 21F | 100 | pH 5.4, 80 mg/mL Tre, F68 0.05 | 4.0 | — | 7.0 |
| 21G | 100 | pH 5, 51 mg/mL Man, F68 0.05 | 3.1 | — | 6.0 |
| 21H | 100 | pH 5, 51 mg/mL Man | 3.7 | — | 6.4 |
| 21I | 100 | pH 4.8, 80 mg/mL Tre, F68 0.05 | 3.9 | 4.9 | — |
| 21L | 100 | pH 5.2, 80 mg/mL Tre, F68 0.05 | 3.5 | 8.0 | — |

TABLE I

% Large aggregates by AUC (40° C.)

| | TACI-Fc5 (mg/mL) | Composition | T = 0 (4 w 5° C.) | 2 w | 3 w |
|---|---|---|---|---|---|
| 21A | 70 | pH 5, 96 mg/mL Tre, F68 0.05 | 2.3 | — | 1.8 |
| 21B | 70 | pH 5, 80 mg/mL Tre | 2.0 | — | 1.5 |
| 21C | 70 | pH 5.4, 80 mg/mL Tre, F68 0.05 | — | — | 2.0 |
| 21D | 100 | pH 5, 80 mg/mL Tre, F68 0.05 | — | — | — |
| 21E | 100 | pH 5, 80 mg/mL Tre | 1.2 | — | 2.8 |
| 21F | 100 | pH 5.4, 80 mg/mL Tre, F68 0.05 | 1.1 | — | 2.6 |
| 21G | 100 | pH 5, 51 mg/mL Man, F68 0.05 | 1.5 | — | 3.0 |
| 21H | 100 | pH 5, 51 mg/mL Man | 1.9 | — | 3.9 |
| 21I | 100 | pH 4.8, 80 mg/mL Tre, F68 0.05 | 1.9 | 5.8 | — |
| 21L | 100 | pH 5.2, 80 mg/mL Tre, F68 0.05 | 2.0 | 4.6 | — |

TABLE J

Protein content by SE-HPLC (2-8° C.)

| | TACI-Fc5 (mg/mL) | Composition | time 0 | 4 w | 6 w | 8 w | 12 w | 16 w | 26 w |
|---|---|---|---|---|---|---|---|---|---|
| 21A | 70 | pH 5, 96 mg/mL Tre, F68 0.05 | 64.7 | 64.2 | 66.3 | 63.2 | 66.9 | | 66.0 |
| 21B | 70 | pH 5, 80 mg/mL Tre | 69.8 | 62.2 | 67.3 | 62.1 | 67.6 | | 63.1 |
| 21C | 70 | pH 5.4, 80 mg/mL Tre, F68 0.05 | 62.1 | 64.7 | 66.4 | 63.7 | 65.7 | | 64.4 |
| 21D | 100 | pH 5, 80 mg/mL Tre, F68 0.05 | 90.7 | 91.5 | 91.8 | 89.1 | 96.8 | | 92.5 |
| 21E | 100 | pH 5, 80 mg/mL Tre | 92.6 | 97.7 | 99.8 | 87.7 | 92.9 | | 92.4 |
| 21F | 100 | pH 5.4, 80 mg/mL Tre, F68 0.05 | 96.1 | 91.8 | 94.3 | 90.4 | 92.8 | | 93.5 |
| 21G | 100 | pH 5, 51 mg/mL Man, F68 0.05 | 94.7 | 100.4 | 95.7 | 91.2 | 93.3 | | 90.4 |
| 21H | 100 | pH 5, 51 mg/mL Man | 89.0 | 98.6 | 90.6 | 89.0 | 93.3 | | 88.8 |
| 21I | 100 | pH 4.8, 80 mg/mL Tre, F68 0.05 | 94.3 | 99.5 | 88.8 | 100.0 | | 91.5 | |
| 21L | 100 | pH 5.2, 80 mg/mL Tre, F68 0.05 | 96.9 | 85.2 | 93.3 | 99.6 | | 98.2 | |

TABLE K

Protein content by SE-HPLC (25° C.)

| | TACI-Fc5 (mg/mL) | Composition | time 0 | 2 w | 4 w | 6 w | 8 w | 12 w | 17 w | 27 w |
|---|---|---|---|---|---|---|---|---|---|---|
| 21A | 70 | pH 5, 96 mg/mL Tre, F68 0.05 | 64.7 | 61.6 | 66.8 | 67.5 | 65.3 | 68.3 | | 63.3 |
| 21B | 70 | pH 5, 80 mg/mL Tre | 69.8 | 60.0 | 63.2 | 66.1 | 63.4 | 64.7 | | 62.7 |
| 21C | 70 | pH 5.4, 80 mg/mL Tre, F68 0.05 | 62.1 | 59.0 | 64.1 | 66.8 | 64.5 | 64.4 | | 62.9 |
| 21D | 100 | pH 5, 80 mg/mL Tre, F68 0.05 | 90.7 | 99.5 | 89.6 | 94.9 | 91.6 | 94.3 | | 89.4 |
| 21E | 100 | pH 5, 80 mg/mL Tre | 92.6 | 85.0 | 91.0 | 98.0 | 92.0 | 95.6 | | 82.1 |
| 21F | 100 | pH 5.4, 80 mg/mL Tre, F68 0.05 | 96.1 | n.v. | 90.9 | 96.0 | 94.5 | 94.4 | | 91.1 |
| 21G | 100 | pH 5, 51 mg/mL Man, F68 0.05 | 94.7 | 88.4 | 96.1 | 92.7 | 105.0 | 93.5 | | 87.8 |
| 21H | 100 | pH 5, 51 mg/mL Man | 89.0 | 88.4 | 94.4 | 94.7 | 89.9 | 91.3 | | 88.5 |
| 21I | 100 | pH 4.8, 80 mg/mL Tre, F68 0.05 | 94.3 | 95.3 | 97.8 | 89.7 | 98.6 | | 95.2 | |
| 21L | 100 | pH 5.2, 80 mg/mL Tre, F68 0.05 | 96.9 | 100.0 | 100.1 | 92.7 | 103.0 | | 92.7 | |

TABLE L

Protein content by SE-HPLC (40° C.)

| | TACI-Fc5 (mg/mL) | Composition | time 0 | 1 w | 2 w | 4 w |
|---|---|---|---|---|---|---|
| 21A | 70 | pH 5, 96 mg/mL Tre, F68 0.05 | 64.7 | 64.9 | 60.9 | 67.1 |
| 21B | 70 | pH 5, 80 mg/mL Tre | 69.8 | 64.5 | 59.8 | 66.9 |
| 21C | 70 | pH 5.4, 80 mg/mL Tre, F68 0.05 | 62.1 | 63.8 | 61.2 | 65.2 |
| 21D | 100 | pH 5, 80 mg/mL Tre, F68 0.05 | 90.7 | 89.3 | 85.7 | 91.4 |
| 21E | 100 | pH 5, 80 mg/mL Tre | 92.6 | 90.5 | 86.2 | 88.6 |

TABLE L-continued

Protein content by SE-HPLC (40° C.)

|   | TACI-Fc5 (mg/mL) | Composition | time 0 | 1 w | 2 w | 4 w |
|---|---|---|---|---|---|---|
| 21F | 100 | pH 5.4, 80 mg/mL Tre, F68 0.05 | 96.1 | 93.5 | 85.1 | 90.7 |
| 21G | 100 | pH 5, 51 mg/mL Man, F68 0.05 | 94.7 | 88.6 | 85.6 | 97.8 |
| 21H | 100 | pH 5, 51 mg/mL Man | 89.0 | 93.0 | 83.9 | 96.5 |
| 21I | 100 | pH 4.8, 80 mg/mL Tre, F68 0.05 | 94.3 | 92.0 | 91.2 | 99.7 |
| 21L | 100 | pH 5.2, 80 mg/mL Tre, F68 0.05 | 96.9 | 97.1 | 94.9 | 103.3 |

TABLE M pH values (2-8° C.)

|   | TACI-Fc5 (mg/mL) | Composition | time 0 | 4 w | 6 w | 8 w | 12 w | 16 w | 26 w |
|---|---|---|---|---|---|---|---|---|---|
| 21A | 70 | pH 5, 96 mg/mL Tre, F68 0.05 | 5.2 | 5.1 | 5.1 | 5.1 | 5.1 | — | 5.1 |
| 21B | 70 | pH 5, 80 mg/mL Tre | 5.2 | 5.1 | 5.1 | 5.1 | 5.1 | — | 5.1 |
| 21C | 70 | pH 5.4, 80 mg/mL Tre, F68 0.05 | 5.4 | 5.3 | 5.3 | 5.3 | 5.3 | — | 5.3 |
| 21D | 100 | pH 5, 80 mg/mL Tre, F68 0.05 | 5.1 | 5.0 | 5.0 | 5.0 | 5.0 | — | 5.0 |
| 21E | 100 | pH 5, 80 mg/mL Tre | 5.1 | 5.0 | 5.1 | 5.0 | 5.1 | — | 5.1 |
| 21F | 100 | pH 5.4, 80 mg/mL Tre, F68 0.05 | 5.5 | 5.4 | 5.4 | 5.4 | 5.3 | — | 5.4 |
| 21G | 100 | pH 5, 51 mg/mL Man, F68 0.05 | 5.2 | 5.1 | 5.1 | 5.1 | 5.1 | — | 5.1 |
| 21H | 100 | pH 5, 51 mg/mL Man | 5.2 | 5.1 | 5.1 | 5.1 | 5.1 | — | 5.1 |
| 21I | 100 | pH 4.8, 80 mg/mL Tre, F68 0.05 | 4.8 | 4.8 | 4.9 | 4.8 | — | 4.8 | — |
| 21L | 100 | pH 5.2, 80 mg/mL Tre, F68 0.05 | 5.2 | 5.2 | 5.3 | 5.2 | — | 5.2 | — |

TABLE N pH values (25° C.)

|   | TACI-Fc5 (mg/mL) | Composition | time 0 | 2 w | 4 w | 6 w | 8 w | 12 w | 17 w | 27 w |
|---|---|---|---|---|---|---|---|---|---|---|
| 21A | 70 | pH 5, 96 mg/mL Tre, F68 0.05 | 5.2 | 5.2 | 5.1 | 5.1 | 5.0 | 5.1 | — | 5.1 |
| 21B | 70 | pH 5, 80 mg/mL Tre | 5.2 | 5.1 | 5.0 | 5.1 | 5.0 | 5.1 | — | 5.1 |
| 21C | 70 | pH 5.4, 80 mg/mL Tre, F68 0.05 | 5.4 | 5.4 | 5.3 | 5.3 | 5.3 | 5.4 | — | 5.3 |
| 21D | 100 | pH 5, 80 mg/mL Tre, F68 0.05 | 5.1 | 5.0 | 5.0 | 5.0 | 5.1 | 5.1 | — | 5.0 |
| 21E | 100 | pH 5, 80 mg/mL Tre | 5.1 | 5.1 | 5.0 | 5.1 | 5.0 | 5.1 | — | 5.0 |
| 21F | 100 | pH 5.4, 80 mg/mL Tre, F68 0.05 | 5.5 | 5.4 | 5.4 | 5.4 | 5.4 | 5.4 | — | 5.3 |
| 21G | 100 | pH 5, 51 mg/mL Man, F68 0.05 | 5.2 | 5.1 | 5.1 | 5.1 | 5.1 | 5.1 | — | 5.1 |
| 21H | 100 | pH 5, 51 mg/mL Man | 5.2 | 5.1 | 5.1 | 5.1 | 5.1 | 5.1 | — | 5.1 |
| 21I | 100 | pH 4.8, 80 mg/mL Tre, F68 0.05 | 4.8 | 4.8 | 4.8 | 4.9 | 4.9 | — | 4.9 | — |
| 21L | 100 | pH 5.2, 80 mg/mL Tre, F68 0.05 | 5.2 | 5.3 | 5.2 | 5.2 | 5.3 | — | 5.2 | — |

TABLE O pH values (40° C.)

|   | TACI-Fc5 (mg/mL) | Composition | time 0 | 1 w | 2 w | 4 w |
|---|---|---|---|---|---|---|
| 21A | 70 | pH 5, 96 mg/mL Tre, F68 0.05 | 5.2 | 5.1 | 5.2 | 5.1 |
| 21B | 70 | pH 5, 80 mg/mL Tre | 5.2 | 5.1 | 5.1 | 5.1 |
| 21C | 70 | pH 5.4, 80 mg/mL Tre, F68 0.05 | 5.4 | 5.4 | 5.4 | 5.4 |
| 21D | 100 | pH 5, 80 mg/mL Tre, F68 0.05 | 5.1 | 5.0 | 5.1 | 5.0 |
| 21E | 100 | pH 5, 80 mg/mL Tre | 5.1 | 5.1 | 5.1 | 5.0 |
| 21F | 100 | pH 5.4, 80 mg/mL Tre, F68 0.05 | 5.5 | 5.4 | 5.4 | 5.4 |
| 21G | 100 | pH 5, 51 mg/mL Man, F68 0.05 | 5.2 | 5.1 | 5.1 | 5.1 |
| 21H | 100 | pH 5, 51 mg/mL Man | 5.2 | 5.1 | 5.1 | 5.1 |
| 21I | 100 | pH 4.8, 80 mg/mL Tre, F68 0.05 | 4.8 | 4.9 | 4.9 | 4.9 |
| 21L | 100 | pH 5.2, 80 mg/mL Tre, F68 0.05 | 5.2 | 5.3 | 5.3 | 5.3 |

TABLE P

| | Osmolality (OSM/kg) | | |
|---|---|---|---|
| | TACI-Fc5 (mg/mL) | Composition | T = 0 |
| 21A | 70 | pH 5, 96 mg/mL Tre, F68 0.05 | 0.444 |
| 21B | 70 | pH 5, 80 mg/mL Tre | 0.359 |
| 21C | 70 | pH 5.4, 80 mg/mL Tre, F68 0.05 | 0.359 |
| 21D | 100 | pH 5, 80 mg/mL Tre, F68 0.05 | 0.409 |
| 21E | 100 | pH 5, 80 mg/mL Tre | 0.414 |
| 21F | 100 | pH 5.4, 80 mg/mL Tre, F68 0.05 | 0.414 |
| 21G | 100 | pH 5, 51 mg/mL Man, F68 0.05 | 0.445 |
| 21H | 100 | pH 5, 51 mg/mL Man | 0.438 |
| 21I | 100 | pH 4.8, 80 mg/mL Tre, F68 0.05 | 0.388 |
| 21L | 100 | pH 5.2, 80 mg/mL Tre, F68 0.05 | 0.368 |

TABLE Q

| | Bioassay (U/mL) (2-8° C.) | | | | | | |
|---|---|---|---|---|---|---|---|
| | TACI-Fc5 (mg/mL) | Composition | Expected | time 0 | 4 w | 8 w | 13 w |
| 21A | 70 | pH 5, 96 mg/mL Tre, F68 0.05 | 350000 | 347704 | 365778 | 319050 | 387896 |
| 21B | 70 | pH 5, 80 mg/mL Tre | 350000 | 336185 | 318012 | 289824 | 357861 |
| 21C | 70 | pH 5.4, 80 mg/mL Tre, F68 0.05 | 350000 | 323222 | 333715 | 306941 | 335181 |
| 21D | 100 | pH 5, 80 mg/mL Tre, F68 0.05 | 500000 | 461204 | 452442 | 431738 | 489743 |
| 21E | 100 | pH 5, 80 mg/mL Tre | 500000 | 458617 | 439084 | 435680 | 470251 |
| 21F | 100 | pH 5.4, 80 mg/mL Tre, F68 0.05 | 500000 | 455676 | 470037 | 407200 | 424278 |
| 21G | 100 | pH 5, 51 mg/mL Man, F68 0.05 | 500000 | 494293 | 543338 | 401277 | 445267 |
| 21H | 100 | pH 5, 51 mg/mL Man | 500000 | 471667 | 446056 | 387503 | 445371 |

TABLE R

| | Bioassay (U/mL) (25° C.) | | | | | | |
|---|---|---|---|---|---|---|---|
| | TACI-Fc5 (mg/mL) | Composition | Expected | time 0 | 4 w | 8 w | 13 w |
| 21A | 70 | pH 5, 96 mg/mL Tre, F68 0.05 | 350000 | 347704 | 311541 | 279159 | 304644 |
| 21B | 70 | pH 5, 80 mg/mL Tre | 350000 | 336185 | 302066 | 268469 | 342827 |
| 21C | 70 | pH 5.4, 80 mg/mL Tre, F68 0.05 | 350000 | 323222 | 315938 | 269441 | 318150 |
| 21D | 100 | pH 5, 80 mg/mL Tre, F68 0.05 | 500000 | 461204 | 508830 | 431335 | 418713 |
| 21E | 100 | pH 5, 80 mg/mL Tre | 500000 | 458617 | 441768 | 396159 | 405400 |
| 21F | 100 | pH 5.4, 80 mg/mL Tre, F68 0.05 | 500000 | 455676 | 449141 | 387455 | 476384 |
| 21G | 100 | pH 5, 51 mg/mL Man, F68 0.05 | 500000 | 494293 | 496542 | 433228 | 440685 |
| 21H | 100 | pH 5, 51 mg/mL Man | 500000 | 471667 | 465114 | 365910 | 433696 |

TABLE S

| C-terminus truncation | | |
|---|---|---|
| Sample | Stability time | Truncated |
| S128/L20a bulk | — | 95.0% |
| 21E | 8 months 2-8° C. | 95.3% |
| 21E | 8 months 25° C. | 94.7% |

TABLE T

| | | Clipped forms | | | |
|---|---|---|---|---|---|
| Sample | Stability time | Peak 1 (Fc fragment) | Peaks 2 + 3 | Peak 4 (Intact) | Total clipping |
| S128/L20a bulk | — | 4.2% | 14.0% | 81.8% | 18.2% |
| 21E | 10 months 2-8° C. | 4.5% | 15.0% | 80.5% | 19.5% |
| 21E | 10 months 25° C. | 8.2% | 37.5% | 54.3% | 45.7% |

Summary of the Main Results

Size Exclusion Chromatography

At 25° C., 70 mg/mL formulations generally showed lower slopes as regards the rate of aggregation (% aggregates/month) than 100 mg/mL ones. In the latter group, formulations 21D and 21E were the ones displaying the lowest slopes.

At 40° C., formulation 21E exhibited the lowest value of slope in the group of 100 mg/mL liquid formulations.

AUC

No change in the AUC profile was observed at 2-8 and 25° C. for formulation 21E. A tendency towards monomer increase over the stability time was detected for the 70 mg/mL formulations.

Unfolding Monitored by CD

In the group of 100 mg/mL formulations, 21E was the one exhibiting the highest Tunf. pH values different from 5.0 lead to lower $T_{unf}$. The 70 mg/mL formulations display higher values of $T_{unf}$ (i.e. higher stability).

Intrinsic Fluorescence

At 40° C., minor variations in the maximum emission wavelength were detected for 70 mg/mL formulations and, in the group of 100 mg/mL candidates, for formulation 21E.

RALS

Noticeable increases in RALS for formulations at pH different from the "optimum" of 5 after storage at 40° C. The scattering of formulations with mannitol was considerably higher than the others. Formulations 21A, 21B, 21D and 21E were those displaying lower values of scattering. After storage at 2-8° C., they did not show any increase in the scattered light.

Anisotropy of Fluorescence Emission

No variations in anisotropy was observed for formulations 21A and 21B after storage at 40° C. (1 month). There were relevant variations for formulations 21F and 21H. In-between variations observed for the others.

Dynamic Light Scattering

At 2-8° C., no relevant variations in size distribution were detected. Some decreases in larger species % was observed after storage at 25° C. No dramatic increases in higher molecular weight species after storage at 40° C. for all formulations except for both those containing mannitol and those at pH different from 5.0

Free Energy of Unfolding

In the group of 100 mg/mL formulations, higher thermodynamic stability was observed for formulations 21D and 21E.

Bioassay

No decreases were observed in the bioactivity over 3 months at 25 and 40° C.

Overall Conclusions

Pre-screening studies on liquid formulations have shown that the optimal pH for the stabilization of 70 mg/mL TACI-Fc5 solutions was around pH 5. The higher the pH values, the stronger were the aggregation phenomena (evaluated by SE-HPLC) and the occurrence of concentration drops (estimated by RP-HPLC and optical density). The presence of salts (such as NaCl, CaCl2 and MgCl2) lead to increases in aggregates as well. Values of pH lower than 5 were not optimal either, as also shown by conformational studies by circular dichroism at pH=4.0 compared to 5.0 in different buffers. Preliminary DSC experiments showed that trehalose and sucrose had some positive effect on the stability of the molecule (i.e. higher unfolding temperatures).

The experimental design phase aimed at investigating the effect of several excipients dissolved in acetate or histidine buffer at pH=5.0 (different buffering strengths were tested as well) in presence of surfactants such as Lutrol® F-68 and Tween20. Low concentrations of acetate buffer in presence of mannitol or trehalose provided the samples with a higher stability against degradation. Lutrol® F-68 appeared to be more effective than Tween 20 in stabilizing the protein.

Fluorescence and dynamic light scattering tests were in agreement with such results.

Candidate samples were manufactured at lab scale at both 70 and 100 mg/mL TACI-Fc concentrations. Trehalose and mannitol were used as excipients (in presence of sodium acetate buffer at pH=4.8, 5.0, 5.2 and 5.4). The evolution of candidates over time has been monitored by SE-HPLC and AUC together with several spectroscopic tools.

From this study, it resulted that lower concentrations of the protein lead to minor aggregation. The optimal pH value was confirmed to be 5.0. Trehalose was more successful than mannitol in stabilizing the TACI-Fc formulations. In the group of 100 mg/mL TACI-Fc candidates, formulation 21E (10 mM sodium acetate, pH=5.0, 80 mg/mL trehalose anhydrous) exhibited a stronger resistance against aggregation at 40° C. (with no statistically relevant increase in aggregation detected at 2-8° C.). More precisely, at 2-8° C. liquid candidate 21E increased its purity by 1.4% in 26 weeks. At 25° C., the purity decreased by only 1% (26 weeks).

The total clipped forms of candidate 21E (10 months at 2-8 and 25° C.) were determined by a RP-HPLC analysis: no variation in the content of clipped forms occurred compared to the starting bulk material (about 19%). C-terminus truncation was found to be about 95%, same as in the starting bulk; this level of truncation is usually observed for human antibodies.

The level of oxidized forms was also checked by RP-MALDI analysis on liquid candidate 21E (stored for 10 months at 2-8 and 25° C.): compared to the bulk drug substance, from which it is prepared, no significant increase in oxidation was observed upon storage (about 2.4%).

EXAMPLE 2

Compatibility of TACI-Fc with Bacteriostatic Agents

Objective:

The aim of this study was to assess the compatibility of TACI-Fc with different bacteriostatic agents in view of a multidose formulation. The following bacteriostatic agents were tested: benzyl alcohol 0.9%; m-cresol 0.3%; phenol 0.5%; chlorobutanol 0.5%; phenylethanol 0.5%; benzyl alcohol 0.3%+benzalkonium chloride 0.001%.

Key Results

Drug Substance+Bacteriostatics:
  Increases (15-70%) in total aggregates (by SEC) were observed, after 2 weeks of storage at 40° C., for the drug substance in presence of preservatives, compared to the reference sample (no bacteriostatic added); comparable degradation rates were observed at 25° C. and 2-8° C.
  The bacteriostatic agent that proved to have the least negative influence (according to SEC and CD analyses) was the mix benzyl alcohol+benzalkonium chloride.

Liquid Candidate+Bacteriostatics:
  The addition of preservatives to the TACI-Fc liquid candidate (acetate pH 5, trehalose) led to less pronounced increases in aggregation (about 10-25%, after 2 weeks at 40° C.) than those observed for the drug substance. This demonstrates the efficacy of trehalose in preventing aggregation and loss of the native secondary structure (as evidenced by far UV CD experiments).
  The association benzyl alcohol+benzalkonium chloride provided the best results, among the group of formulations in presence of preservatives, in terms of aggregation rate.

Conclusion

The impact of several bacteriostatic agents on the protein integrity was evaluated on TACI-Fc drug substance (native bulk) and on formulated TACI-Fc at 100 mg/mL formulated in Na-Acetate and trehalose at pH 5.

The inclusion of any of the bacteriostatic agents negatively affected the protein integrity in particular on native bulk drug substance. The association 0.3% benzyl alcohol+0.001% benzalkonium chloride turned out to be the least detrimental to the protein structure.

EXAMPLE 3

Stability OF TACI-Fc Liquid Candidate in Pre-Filled Syringes

Objective

The aim of the study was to assess the stability of the liquid formulation of TACI-Fc (Na-Acetate, Trehalose, pH 5) at 100 mg/mL filled into 1 mL Hypak syringes stoppered with two types of rubber plungers (W4023/50 and W4023/50G FluoroTec).

Key Results

The results can be summarized as follows for TACI-Fc 100 mg/mL filled into 1 mL glass syringes stoppered with coated (W4023/50G FluoroTec) and uncoated (W4023/50G) plungers, tested up to 6 months:

- Dimers and HMWs: the degradation rate was comparable at 40° C. (1.6% increase/week) and 25° C. (0.5% increase/month). A slightly different behavior was observed at 2-8° C., although not significantly impacting the overall stability: 0.2% and 0.1% increase/month for two different manufacturing batches;
- Protein content: no decrease in the protein content was observed upon storage;
- Clipped forms: a comparable level in clipped forms was measured vs the product in vials (no increase at 2-8° C. compared to the drug substance; about 40% at 25° C. after 5 months);
- Biopotency: the biological activity is retained up to 3 months (2-8° C. and 25° C.)
- pH: no pH shift was observed upon storage.

Conclusion

The liquid formulation of TACI-Fc at 100 mg/mL (acetate buffer pH 5+trehalose) filled into 1 mL Hypak syringes was stable. The two types of rubber plungers (W4023/50 and W4023/50G FluoroTec) evaluated in the study were equivalent and did not affect the stability of the liquid formulation.

EXAMPLE 4

Stability of Atacicept at Different Strengths in Pre-Filled Syringes

The stability of atacicept at different strengths in pre-filled syringes was assessed. The methodology was carried out as reported in Example 1.

The composition of the tested samples was as follows:

| Batch ID | Atacicept mg/mL | Buffer | Trehalose dihydrate mg/mL |
|---|---|---|---|
| Atacicept 25/1 | 25 | 10 mM sodium acetate, pH 5 | 88.4 |
| Atacicept 75/1 | 75 | 10 mM sodium acetate, pH 5 | 88.4 |
| Atacicept 150/1 | 150 | 10 mM sodium acetate, pH 5 | 88.4 |
| Atacicept 25/1.2 | 20.5 | 10 mM sodium acetate, pH 5 | 88.4 |
| Atacicept 150/1.2 | 125 | 10 mM sodium acetate, pH 5 | 88.4 |

The results from the stability study are reported in the following tables U to Z.

TABLE U

% Purity by SE-HPLC

At 5° C., after 1, 2, 3, 6, 9, 12 and 18 months:

| | Zero Time | | | 1 month +5° C. | | |
|---|---|---|---|---|---|---|
| | HMW + Dimer | M | LMW | HMW + Dimer | M | LMW |
| Atacicept 25/1 | 0.4 | 99.0 | 0.5 | 0.4 | 99.2 | 0.4 |
| Atacicept 75/1 | 0.5 | 99.0 | 0.5 | 0.6 | 99.1 | 0.3 |
| Atacicept 150/1 | 0.5 | 99.0 | 0.5 | 0.7 | 98.8 | 0.4 |
| Atacicept 25/1.2 | 0.5 | 99.1 | 0.4 | 0.5 | 99.1 | 0.4 |
| Atacicept 150/1.2 | 0.6 | 99.0 | 0.4 | 0.7 | 98.9 | 0.5 |

| | 2 months +5° C. | | | 3 months +5° C. | | |
|---|---|---|---|---|---|---|
| | HMW + Dimer | M | LMW | HMW + Dimer | M | LMW |
| Atacicept 25/1 | 0.4 | 99.2 | 0.4 | 0.4 | 99.1 | 0.5 |
| Atacicept 75/1 | 0.6 | 99.1 | 0.3 | 0.6 | 99.2 | 0.3 |
| Atacicept 150/1 | 0.8 | 98.7 | 0.5 | 1.0 | 98.4 | 0.7 |
| Atacicept 25/1.2 | 0.5 | 99.2 | 0.3 | 0.4 | 98.7 | 1.0 |
| Atacicept 150/1.2 | 0.7 | 98.8 | 0.5 | 0.6 | 98.9 | 0.6 |

| | 6 months +5° C. | | | 9 months +5° C. | | |
|---|---|---|---|---|---|---|
| | HMW + Dimer | M | LMW | HMW + Dimer | M | LMW |
| Atacicept 25/1 | 0.4 | 99.3 | 0.4 | 0.3 | 99.3 | 0.4 |
| Atacicept 75/1 | 0.7 | 99.0 | 0.4 | 0.8 | 98.9 | 0.3 |
| Atacicept 150/1 | 1.1 | 98.7 | 0.3 | 1.2 | 98.4 | 0.4 |
| Atacicept 25/1.2 | 0.3 | 99.3 | 0.4 | 0.4 | 99.3 | 0.4 |
| Atacicept 150/1.2 | 0.8 | 98.7 | 0.4 | 1.0 | 98.5 | 0.5 |

| | 12 months +5° C. | | | 18 months +5° C. | | |
|---|---|---|---|---|---|---|
| | HMW + Dimer | M | LMW | HMW + Dimer | M | LMW |
| Atacicept 25/1 | 0.3 | 99.2 | 0.4 | 0.4 | 99.3 | 0.3 |
| Atacicept 75/1 | 0.9 | 98.9 | 0.3 | | | |
| Atacicept 150/1 | 1.3 | 98.2 | 0.5 | 1.9 | 97.8 | 0.4 |
| Atacicept 25/1.2 | 0.4 | 99.2 | 0.4 | 0.4 | 99.3 | 0.3 |
| Atacicept 150/1.2 | 1.3 | 98.3 | 0.5 | 1.6 | 97.9 | 0.5 |

TABLE U-continued

% Purity by SE-HPLC

At 25° C., after 1, 2, 3 and 6 months:

|  | Zero Time | | | 1 month +25° C. | | | 2 months +25° C. | | |
| --- | --- | --- | --- | --- | --- | --- | --- | --- | --- |
|  | HMW + Dimer | M | LMW | HMW + Dimer | M | LMW | HMW + Dimer | M | LMW |
| Atacicept 25/1 | 0.4 | 99.0 | 0.5 | 0.4 | 98.9 | 0.7 | 0.4 | 98.8 | 0.8 |
| Atacicept 75/1 | 0.5 | 99.0 | 0.5 | 0.9 | 98.5 | 0.6 | 1.4 | 97.8 | 0.8 |
| Atacicept 150/1 | 0.5 | 99.0 | 0.5 | 2.0 | 97.1 | 0.9 | 2.8 | 96.1 | 1.2 |
| Atacicept 25/1.2 | 0.5 | 99.1 | 0.4 | 0.4 | 99.0 | 0.6 | 0.3 | 98.8 | 0.9 |
| Atacicept 150/1.2 | 0.6 | 99.0 | 0.4 | 1.5 | 97.7 | 0.9 | 2.3 | 96.3 | 1.4 |

|  | 3 months +25° C. | | | 6 months +25° C. | | |
| --- | --- | --- | --- | --- | --- | --- |
|  | HMW + Dimer | M | LMW | HMW + Dimer | M | LMW |
| Atacicept 25/1 | 0.4 | 98.5 | 1.1 | 0.4 | 98.2 | 1.4 |
| Atacicept 75/1 | 1.6 | 97.7 | 0.7 | 2.6 | 96.1 | 1.3 |
| Atacicept 150/1 | 3.7 | 94.8 | 1.5 | 5.8 | 92.1 | 2.1 |
| Atacicept 25/1.2 | 0.3 | 98.5 | 1.2 | 0.3 | 98.4 | 1.3 |
| Atacicept 150/1.2 | 2.5 | 96.0 | 1.5 | 4.3 | 94.1 | 1.6 |

TABLE V

Protein Content by SE-HPLC (mg/mL)

At 5° C., after 1, 2, 3, 6, 9, 12 and 18 months:

|  | Zero Time | 1 Mo +5° C. | 2 Mo +5° C. | 3 Mo +5° C. |
| --- | --- | --- | --- | --- |
| Atacicept 25/1 | 23.9 | 27.9 | 22.7 | 21.9 |
| Atacicept 75/1 | 75.0 | 80.4 | 77.9 | 76.6 |
| Atacicept 150/1 | 150.0 | 165.5 | 160.2 | 161.0 |
| Atacicept 25/1.2 | 21.8 | 24.3 | 23.6 | 22.0 |
| Atacicept 150/1.2 | 138.1 | 138.4 | 144.9 | 148.5 |

|  | 6 Mo +5° C. | 9 Mo +5° C. | 12 Mo +5° C. | 18 Mo +5° C. |
| --- | --- | --- | --- | --- |
| Atacicept 25/1 | 25.1 | 24.9 | 26.1 | 25.2 |
| Atacicept 75/1 | 80.1 | 78.8 | 77.2 | |
| Atacicept 150/1 | 156.5 | 152.0 | 157.9 | 152.1 |
| Atacicept 25/1.2 | 22.3 | 21.3 | 22.2 | 21.6 |
| Atacicept 150/1.2 | 136.3 | 134.1 | 132.4 | 126.1 |

At 25° C., after 1, 2, 3 and 6 months:

|  | Zero Time | 1 Mo+25° C. | 2 Mo+25° C. | Mo+25° C. | 6 Mo+25° C. |
| --- | --- | --- | --- | --- | --- |
| Atacicept 25/1 | 23.9 | 28.0 | 21.5 | 21.9 | 25.1 |
| Atacicept 75/1 | 75.0 | 80.1 | 77.4 | 73.5 | 79.8 |
| Atacicept 150/1 | 150.0 | 163.8 | 165.5 | 162.8 | 152.2 |
| Atacicept 25/1.2 | 21.8 | 22.9 | 23.4 | 21.3 | 21.6 |
| Atacicept 150/1.2 | 138.1 | 141.6 | 137.2 | 147.7 | 128.6 |

At 40° C., after 1, 2 and 4 weeks:

|  | Zero Time | 1 wk +40° C. | 2 wk +40° C. | 4 wk +40° C. |
| --- | --- | --- | --- | --- |
| Atacicept 75/1 | 75.0 | 71.7 | 71.9 | 71.8 |

TABLE W

Clipped forms (%)

At 5° C., after 1, 2, 3, 6, 9, 12 and 18 months:

|  | Zero Time | 1 Mo +5° C. | 2 Mo +5° C. | 3 Mo +5° C. |
| --- | --- | --- | --- | --- |
| Atacicept 25/1 | 11.0 | 12.8 | 12.8 | 12.5 |
| Atacicept 75/1 | 11.6 | 13.8 | 12.1 | 13.0 |
| Atacicept 150/1 | 11.5 | 12.3 | 13.5 | 13.1 |
| Atacicept 25/1.2 | 12.7 | 12.7 | 12.8 | 13.5 |
| Atacicept 150/1.2 | 12.3 | 13.0 | 12.5 | 14.1 |

TABLE W-continued

| Clipped forms (%) | | | | |
|---|---|---|---|---|
| | 6 Mo +5° C. | 9 Mo +5° C. | 12 Mo +5° C. | 18 Mo +5° C. |
| Atacicept 25/1 | 14.1 | 14.7 | 15.4 | 18.4 |
| Atacicept 75/1 | 13.5 | 15.4 | 16.7 | |
| Atacicept 150/1 | 14.3 | 16.1 | 16.7 | 19.3 |
| Atacicept 25/1.2 | 15.9 | 15.8 | 16.9 | 18.5 |
| Atacicept 150/1.2 | 15.4 | 16.5 | 18.6 | 18.7 |

| At 25° C., after 1, 2, 3 and 6 months: | | | | | |
|---|---|---|---|---|---|
| | Zero Time | 1 Mo+25° C. | 2 Mo+25° C. | 3 Mo+25° C. | 6 Mo+25° C. |
| Atacicept 25/1 | 11.0 | 17.5 | 20.1 | 25.8 | 32.8 |
| Atacicept 75/1 | 11.6 | 17.4 | 20.4 | 24.1 | 33.8 |
| Atacicept 150/1 | 11.5 | 18.3 | 21.7 | 26.7 | 35.1 |
| Atacicept 25/1.2 | 12.7 | 16.7 | 20.6 | 25.4 | 34.9 |
| Atacicept 150/1.2 | 12.3 | 17.1 | 22.1 | 26.7 | 37.3 |

TABLE X

| % Free-Fc by IEC-HPLC | | | | |
|---|---|---|---|---|
| At 5° C., after 1, 2, 3, 6, 9, 12 and 18 months: | | | | |
| | Zero Time | 1 Mo +5° C. | 2 Mo +5° C. | 3 Mo +5° C. |
| Atacicept 25/1 | — | 0.08 | 0.08 | 0.08 |
| Atacicept 75/1 | 0.09 | 0.14 | 0.14 | 0.11 |
| Atacicept 150/1 | — | 0.09 | 0.09 | 0.10 |
| Atacicept 25/1.2 | 0.09 | 0.08 | 0.09 | 0.09 |
| Atacicept 150/1.2 | 0.08 | 0.09 | 0.11 | 0.13 |
| | 6 Mo +5° C. | 9 Mo +5° C. | 12 Mo +5° C. | 18 Mo +5° C. |
| Atacicept 25/1 | 0.18 | 0.13 | 0.12 | 0.12 |
| Atacicept 75/1 | 0.12 | 0.13 | 0.12 | |
| Atacicept 150/1 | 0.19 | 0.16 | 0.15 | 0.16 |
| Atacicept 25/1.2 | 0.11 | 0.11 | 0.12 | 0.11 |
| Atacicept 150/1.2 | 0.13 | 0.17 | 0.15 | 0.16 |

| At 25° C., after 1, 2, 3 and 6 months: | | | | | |
|---|---|---|---|---|---|
| | Zero Time | 1 Mo+25° C. | 2 Mo+25° C. | 3 Mo+25° C. | 6 Mo+25° C. |
| Atacicept 25/1 | — | 0.17 | 0.22 | 0.40 | 0.77 |
| Atacicept 75/1 | 0.09 | 0.25 | 0.39 | 0.43 | 0.72 |
| Atacicept 150/1 | — | 0.20 | 0.32 | 0.52 | 0.87 |
| Atacicept 25/1.2 | 0.09 | 0.13 | 0.30 | 0.49 | 0.70 |
| Atacicept 150/1.2 | 0.08 | 0.18 | 0.38 | 0.51 | 0.81 |

TABLE Y

| Biological activity (U/mL) | | | | |
|---|---|---|---|---|
| At 5° C., after 1, 2, 3, 6, 9, 12 and 18 months: | | | | |
| | Zero Time | 1 Mo +5° C. | 2 Mo +5° C. | 3 Mo +5° C. |
| Atacicept 25/1 | 140213 | 137160 | 134504 | 135542 |
| Atacicept 75/1 | 423184 | 410261 | 379575 | 374383 |
| Atacicept 150/1 | 836070 | 774584 | 754834 | 819172 |
| Atacicept 25/1.2 | 111981 | 115990 | 126041 | 121648 |
| Atacicept 150/1.2 | 646679 | 642858 | 743090 | 694864 |
| | 6 Mo +5° C. | 9 Mo +5° C. | 12 Mo +5° C. | 18 Mo +5° C. |
| Atacicept 25/1 | 126923 | 147341 | 130609 | 108207 |
| Atacicept 75/1 | 363668 | 468484 | 346080 | |
| Atacicept 150/1 | 814539 | 843419 | 809840 | 565084 |
| Atacicept 25/1.2 | 114946 | 123750 | 106004 | 113312 |
| Atacicept 150/1.2 | 645404 | 714223 | 620301 | 550851 |

TABLE Y-continued

| | Biological activity (U/mL) | | | | |
|---|---|---|---|---|---|
| | At 25° C., after 1, 2, 3 and 6 months: | | | | |
| | Zero Time | 1 Mo+25° C. | 2 Mo+25° C. | 3 Mo+25° C. | 6 Mo+25° C. |
| Atacicept 25/1 | 140213 | 134212 | 124601 | 132349 | 118224 |
| Atacicept 75/1 | 423184 | 387654 | 336790 | 365202 | 327925 |
| Atacicept 150/1 | 836070 | 776645 | 719725 | 760795 | 677110 |
| Atacicept 25/1.2 | 111981 | 114068 | 117615 | 114296 | 103328 |
| Atacicept 150/1.2 | 646679 | 694993 | 696945 | 606957 | 586586 |

TABLE Z

| | pH determination | | | |
|---|---|---|---|---|
| | At 5° C.,, after 1, 2 and 3 months: | | | |
| | Zero Time | 1 Mo +5° C. | 2 Mo +5° C. | 3 Mo +5° C. |
| Atacicept 25/1 | 5.0 | 5.0 | 4.9 | 4.9 |
| Atacicept 75/1 | 5.1 | 5.1 | 5.1 | 5.1 |
| Atacicept 150/1 | 5.0 | 5.1 | 5.0 | 4.9 |
| Atacicept 25/1.2 | 5.0 | 4.9 | 4.9 | 4.8 |
| Atacicept 150/1.2 | 5.0 | 5.0 | 4.9 | 4.9 |
| | 6 Mo +5° C. | 9 Mo +5° C. | 12 Mo +5° C. | 18 Mo +5° C. |
| Atacicept 25/1 | 5.0 | 4.9 | 5.1 | 4.9 |
| Atacicept 75/1 | 5.0 | 5.1 | 5.1 | |
| Atacicept 150/1 | 5.1 | 5.0 | 5.2 | 5.0 |
| Atacicept 25/1.2 | 4.9 | 4.9 | 5.0 | 5.0 |
| Atacicept 150/1.2 | 5.0 | 5.0 | 5.0 | 5.0 |
| | At 25° C., after 1, 2, 3 and 6 months: | | | | |
| | Zero Time | 1 Mo+25° C. | 2 Mo+25° C. | 3 Mo+25° C. | 6 Mo+25° C. |
| Atacicept 25/1 | 5.0 | 4.9 | 4.9 | 4.9 | 5.0 |
| Atacicept 75/1 | 5.1 | 5.1 | 5.1 | 5.1 | 5.1 |
| Atacicept 150/1 | 5.0 | 5.0 | 5.0 | 4.9 | 5.1 |
| Atacicept 25/1.2 | 5.0 | 4.9 | 4.9 | 4.8 | 4.9 |
| Atacicept 150/1.2 | 5.0 | 5.0 | 4.9 | 4.9 | 5.0 |

EXAMPLE 5

Production of BLyS Antagonist

Four amino terminal truncated versions of TACI-Fc were generated. All four had a modified human tissue plasminogen activator signal sequence as disclosed in WO 02/094852 (SEQ ID NO: 25) fused to amino acid residue number 30 of SEQ ID NO: 6. However, the four proteins differed in the location of point in which the "Fc5" was fused to the TACI amino acid sequence of SEQ ID NO: 6. Table 1 outlines the structures of the four fusion proteins.

TABLE 1

| TACI Fc Fusion Proteins | |
|---|---|
| Designation of TACI-Fc | TACI amino acid residues |
| TACI(d1-29)-Fc5 | 30 to 154 of SEQ ID NO: 6 |
| TACI(d1-29, d107-154)-Fc5 | 30 to 106 of SEQ ID NO: 6 |
| TACI(d1-29, d111-154)-Fc5 | 30 to 110 of SEQ ID NO: 6 |
| TACI(d1-29, d120-154)-Fc5 | 30 to 119 of SEQ ID NO: 6 |

Protein encoding expression cassettes were generated by overlap PCR using standard techniques (see, for example, Horton et al., 1989). A nucleic acid molecule encoding TACI and a nucleic acid molecule encoding Fc5 were used as PCR templates. Oligonucleotide primers are identified in Tables 2 and 3.

TABLE 2

| Oligonucleotide Primers Used to Produce TACI Fusion Proteins | | | | |
|---|---|---|---|---|
| | Oligonucleotide Designations | | | |
| Designation of TACI-Fc | 5' TACI | 3' TACI | 5' Fc5 | 3' Fc5 |
| TACI(d1-29)-Fc5 | ZC24,903 | ZC24,955 | ZC24,952 | ZC24,946 |
| TACI(d1-29, d107-154)-Fc5 | ZC24,903 | ZC24,951 | ZC24,949 | ZC24,946 |
| TACI(d1-29, d111-154)-Fc5 | ZC24,903 | ZC28,978 | ZC28,979 | ZC24,946 |
| TACI(d1-29, d120-154)-Fc5 | ZC24,903 | ZC28,981 | ZC28,980 | ZC24,946 |

TABLE 3

Oligonucleotide Sequences

| Primer | Nucleotide Sequence | SEQ ID NO. |
|---|---|---|
| ZC24,903 | 5' TATTAGGCCGGCCACCATGGATGCAATGA 3' | 15 |
| ZC24,955 | 5' TGAAGATTTGGGCTCCTTGAGACCTGGGA 3' | 16 |
| ZC24,952 | 5' TCCCAGGTCTCAAGGAGCCCAAATCTTCA 3' | 17 |
| ZC24,946 | 5' TAATTGGCGCGCCTCTAGATTATTTACCCGGAGACA 3' | 18 |
| ZC24,951 | 5' TGAAGATTTGGGCTCGTTCTCACAGAAGTA 3' | 19 |
| ZC24,949 | 5' ATACTTCTGTGAGAACGAGCCCAAATCTTCA 3' | 20 |
| ZC28,978 | 5' TTTGGGCTCGCTCCTGAGCTTGTTCTCACA 3' | 21 |
| ZC28,979 | 5' CTCAGGAGCGAGCCCAAATCTTCAGACA 3' | 22 |
| ZC28,981 | 5' TTTGGGCTCCCTGAGCTCTGGTGGAA 3' | 23 |
| ZC28,980 | 5' GAGCTCAGGGAGCCCAAATCTTCAGACA 3' | 24 |

The first round of PCR amplifications consisted of two reactions for each of the four amino terminal truncated versions. The two reactions were performed separately using the 5' and 3' TACI oligonucleotides in one reaction, and the 5' and 3' Fc5 oligonucleotides in another reaction for each version. The conditions of the first round PCR amplification were as follows. To a 25 µl final volume was added approximately 200 ng template DNA, 2.5 µl 10×Pfu reaction Buffer (Stratagene), 2 µl of 2.5 mM dNTPs, 0.5 µl of 20 µM each 5' oligonucleotide and 3' oligonucleotide, and 0.5 µl Pfu polymerase (2.5 units, Stratagene). The amplification thermal profile consisted of 94° C. for 3 minutes, 35 cycles at 94° C. for 15 seconds, 50° C. for 15 seconds, 72° C. for 2 minutes, followed by a 2 minute extension at 72° C. The reaction products were fractionated by agarose gel electrophoresis, and the bands corresponding to the predicted sizes were excised from the gel and recovered using a QIAGEN QIAQUICK Gel Extraction Kit (Qiagen), according to the manufacturer's instructions.

The second round of PCR amplification, or overlap PCR amplification reaction, was performed using the gel purified fragments from the first round PCR as DNA template. The conditions of the second round PCR amplification were as follows. To a 25 µl final volume was added approximately 10 ng template DNA each of the TACI fragment and the Fc5 fragment, 2.5 µl 10×Pfu reaction Buffer (Stratagene), 2 µl of 2.5 mM dNTPs, 0.5 µl of 20 µM each ZC24,903 (SEQ ID NO: 15) and ZC24,946 (SEQ ID NO: 18) and 0.5 µl Pfu polymerase (2.5 units, Stratagene). The amplification thermal profile consisted of 94° C. for 1 minute, 35 cycles at 94° C. for 15 seconds, 55° C. for 15 seconds, 72° C. for 2 minutes, followed by a 2 minute extension at 72° C. The reaction products were fractionated by agarose gel electrophoresis, and the bands corresponding to the predicted sizes were excised from the gel and recovered using a QIAGEN QIAQUICK Gel Extraction Kit (Qiagen), according to the manufacturer's instructions.

Each of the four versions of the amino terminal truncated TACI-Fc PCR products were separately cloned using Invitrogen's ZEROBLUNT TOPO PCR Cloning Kit following the manufacturer's recommended protocol. Table 4 identifies the nucleotide and amino acid sequences of these TACI-Fc constructs.

TABLE 4

Sequences of TACI-Fc Variants

| Designation of TACI-Fc | SEQ ID Nos. Nucleotide | Amino Acid |
|---|---|---|
| TACI(d1-29)-Fc5 | 7 | 8 |
| TACI(d1-29, d107-154)-Fc5 | 9 | 10 |
| TACI(d1-29, d111-154)-Fc5 | 11 | 12 |
| TACI(d1-29, d120-154)-Fc5 | 13 | 14 |

After the nucleotide sequences were verified, plasmids comprising each of the four versions of the amino terminal truncated TACI-Fc fusions were digested with FseI and AscI to release the amino acid encoding segments. The FseI-AscI fragments were ligated into a mammalian expression vector containing a CMV promoter and an SV40 poly A segment. Expression vectors were introduced into Chinese hamster ovary cells as described below.

EXAMPLE 6

Production of TACI-Fc Proteins by Chinese Hamster Ovary Cells

The TACI-Fc expression constructs were used to transfect, via electroporation, suspension-adapted Chinese hamster ovary (CHO) DG44 cells grown in animal protein-free medium (Urlaub et al., 1986). CHO DG44 cells lack a functional dihydrofolate reductase gene due to deletions at both dihydrofolate reductase chromosomal locations. Growth of the cells in the presence of increased concentrations of methotrexate results in the amplification of the dihydrofolate reductase gene, and the linked recombinant protein-encoded gene on the expression construct.

CHO DG44 cells were passaged in PFCHO media (JRH Biosciences, Lenexa, Kans.), 4 mM L-Glutamine (JRH Biosciences), and 1× hypothanxine-thymidine supplement (Life Technologies), and the cells were incubated at 37° C. and 5% $CO_2$ in Corning shake flasks at 120 RPM on a rotating shaker platform. The cells were transfected separately with linearized expression plasmids. To ensure sterility, a single ethanol precipitation step was performed on ice for 25 minutes by combining 200 µg of plasmid DNA in an Eppendorf tube with 20 µL of sheared salmon sperm carrier DNA (5'→3' Inc. Boulder, Colo., 10 mg/mL), 22 µL of 3M NaOAc (pH 5.2), and 484 µl of 100% ethanol (Gold Shield Chemical Co., Hayward, Calif.). After incubation, the tube was centrifuged at 14,000 RPM in a microfuge placed in a 4° C. cold room, the supernatant removed and the pellet washed twice with 0.5 mL of 70% ethanol and allowed to air dry.

The CHO DG44 cells were prepared while the DNA pellet was drying by centrifuging $10^6$ total cells (16.5 mL) in a 25 mL conical centrifuge tube at 900 RPM for 5 minutes. The CHO DG44 cells were resuspended into a total volume of 300 µl of PFCHO growth media, and placed in a Gene-Pulser Cuvette with a 0.4 cm electrode gap (Bio-Rad). The DNA, after approximately 50 minutes of drying time, was resuspended into 500 µl of PFCHO growth media and added to the cells in the cuvette so that the total volume did not exceed 800 µl and was allowed to sit at room temperature for 5 minutes to decrease bubble formation. The cuvette was placed in a Bio-Rad Gene Pulser II unit set at 0.296 kV (kilovolts) and 0.950 HC (high capacitance) and electroporated immediately.

The cells were incubated 5 minutes at room temperature before placement in 20 mL total volume of PFCHO media in a CoStar T-75 flask. The flask was placed at 37° C. and 5% $CO_2$ for 48 hours when the cells were then counted by hemocytometer utilizing trypan blue exclusion and put into PFCHO selection media without hypothanxine-thymidine supplement and containing 200 mM methotrexate (Cal Biochem).

Upon recovery of the methotrexate selection process, the conditioned media containing the secreted TACI-Fc proteins were examined by Western Blot analysis.

REFERENCES

Altschul S F et al, J Mol Biol, 215, 403-410, 1990.
Altschul S F et al, Nucleic Acids Res., 25:389-3402, 1997.
Armour K L. et al., 1999. Recombinant human IgG molecules lacking Fcgamma receptor I binding and monocyte triggering activities. Eur J. Immunol. 29(8):2613-24
Canfield S M, Morrison S L. The binding affinity of human IgG for its high affinity Fc receptor is determined by multiple amino acids in the CH2 domain and is modulated by the hinge region. J Exp Med 1991; 173:1483-1491.
Cheema et al. Arthritis Rheum 2001; 44(6): 1313-1319.
Devereux J et al, Nucleic Acids Res, 12, 387-395, 1984.
Do R K G, Hatada E, Lee H, Tourigny M R, Hilbert D, Chen-Kiang S. Attenuation of apoptosis underlies B lymphocyte stimulator enhancement of humoral immune response. J Exp Med 2000; 192(7):953-964.
Duncan et al., Nature 332:563 (1988).
Grantham et al., Science, Vol. 185, pp. 862-864 (1974).
Groom et al. J Clin Invest 2002; 109(I):59-68; Mariette X, Ann Rheum Dis 2003; 62(2):168-171.
Gross et al. Nature 2000; 404:995-999;
Horton et al., Gene 77:61 (1989).
Kabat E A, Glusman M, Knaub V. Quantitative estimation of the albumin and gamma globulin in normal and pathologic cerebrospinal fluid by immunochemical methods. Am J Med 1948; 4:653-662.
Kabat, E. A., Wu, T. T., Perry, H. M., Gottesman, K. S., and Foeller, C. (1991), Sequences of Proteins of Immunological Interest, 5th Ed., National Institutes of Health, Bethesda, Md.
Kalled S L. The role of BAFF in immune function and implications for autoimmunity. Immunol Rev 2005; 204:43-54.
Mackay et al. J Exp Me 1999; 190(11); 1697-1710.
Marsters S A, Yan M, Pitti R M, Haas P E, Dixit V M, Ashkenazi A. Interaction of the TNF homologues BLyS and APRIL with the TNF receptor homologues BCMA and TACI. Curr Biol 2000; 10(13):785-788.
Moore et al. Science 1999; 285(5425): 260-263; Schneider et al. J Exp Med 1999; 189(11): 1747-1756; Do et al. J Exp Med 2000; 192(7):953-964.
Pearson, Methods Enzymol. 1990; 183:63-98.
Roschke V, Sosnovtseva S, Ward C D, Hong J S, Smith R, Albert V et al. BLyS and APRIL form biologically active heterotrimers that are expressed in patients with systemic immune-based rheumatic diseases. J Immunol 2002; 169: 4314-4321.
Rudick et al., Neurology 2001; 56:1324-1330.
Schneider P, Mackay F, Steiner V, Hofmann K, Bodmer J-L, Holler N. BAFF, a novel ligand of the tumor necrosis factor family, stimulates B cell growth. J Exp Med 1999; 189(11): 1747-1756.
Shields R L. et al., 2001. High resolution mapping of the binding site on human IgG1 for Fc gamma RI, Fc gamma RII, Fc gamma RIII, and FcRn and design of IgG1 variants with improved binding to the Fc gamma R. J Biol Chem. 276(9): 6591-604.
Soderstrom M, Link H, Xu Z, Fredriksson S. Optic neuritis and multiple sclerosis: Anti-MBP and anti-MBP peptide antibody-secreting cells are accumulated in CSF. Neurology 1993; 43:1215-1222.
Sondermann et al., Nature 406:267 (2000).
Tao M-H, Smith R I F, Morrison S L. Structural features of human immunoglobulin G that determine isotype-specific differences in complement activation. J Exp Med 1993; 178:661-667.
Thangarajh M, Gomes A, Masterman T, Hillert J, Hjelmstrom P. Expression of B-cell activating factor of the TNF family (BAFF) and its receptors in multiple sclerosis. J Neuroimmunol 2004; 152:183-190.
Thompson J S, Bixler S A, Qian F, Vora K, Scott M L, Cachero T G. BAFF-R, a newly identified TNF receptor that specifically interacts with BAFF. Science 2001; 293:2108-2111.
Urlaub et al., Som. Cell. Molec. Genet. 12:555 (1986).
Wines et al., J. Immunol. 164:5313 (2000).

The invention claimed is:

1. A pharmaceutical composition comprising:
   a. a therapeutically active TACI-immunoglobulin (TACI-Ig) fusion protein comprising the sequence set forth in SEQ ID NO:3;
   b. an acetate buffer buffering the formulation at a pH ranging between 4.9 and 5.1; and,
   c. trehalose in a concentration ranging from 60 to 100 mg/ml.

2. The pharmaceutical composition according to claim 1, having a pH of 5.0.

3. The pharmaceutical composition according to claim 1, wherein said acetate buffer is sodium acetate.

4. The pharmaceutical composition according to claim 3, wherein said sodium acetate has a concentration of 5 to 25 mM.

5. The pharmaceutical composition according to claim 1, wherein said trehalose is in a concentration of 80 mg/ml.

6. The pharmaceutical composition according to claim 1, wherein the concentration of said TACI-Ig fusion protein is comprised between 70 and 180 mg/mL, the concentration of said trehalose is comprised between 80 and 100 mg/mL, and wherein said buffer is a 10 mM sodium acetate buffer.

7. The pharmaceutical composition according to claim 1, further comprising a preservative.

8. The pharmaceutical composition according to claim 7, wherein the preservative is a combination of benzyl alcohol and benzalconium chloride.

9. The pharmaceutical composition according to claim 1, wherein said TACI-Ig fusion protein is in a concentration ranging from 20 mg/mL to 180 mg/mL.

10. The pharmaceutical composition according to claim 1, wherein the formulation is in liquid form.

11. A process for the preparation of a pharmaceutical composition comprising a therapeutically active TACI-immunoglobulin (TACI-Ig) fusion protein comprising the step of preparing a liquid solution of a TACI-Ig fusion protein in an acetate buffer and adjusting the pH of said liquid solution in the range between 4.9 to 5.1 and adjusting the trehalose concentration to a range between 60 to 100 mg/ml; wherein said TACI-Ig fusion protein comprises the sequence set forth in SEQ ID NO:3.

12. The process for preparation of a pharmaceutical composition according to claim 11, further comprising the step of placing a predetermined amount of the pharmaceutical composition into a sterile container.

13. The process according to claim 12, wherein said container is a glass vial or a pre-filled syringe.

14. The pharmaceutical composition of claim 1, wherein said acetate buffer is in a concentration of 5 to 25 mM.

15. The pharmaceutical composition of claim 14, wherein said acetate buffer is in a concentration of 10 mM.

16. The pharmaceutical composition of claim 9, wherein said TACI-Ig fusion protein is in a concentration of 70, 75, 100, 125 or 150 mg/ml.

17. The pharmaceutical composition of claim 1, wherein said pharmaceutical composition comprises said TACI-Ig fusion protein in a concentration between 70 and 180 mg/ml and acetate buffer in a concentration of 10 mM.

18. The method of claim 11, wherein the pH of said liquid solution is adjusted to a pH of 5.0.

19. The method of claim 11, wherein said acetate buffer is sodium acetate.

20. The method of claim 19, wherein said sodium acetate has a concentration of 5 to 25 mM.

21. The method of claim 11, wherein the concentration of said TACI-Ig fusion protein is between 70 and 180 mg/mL, the said trehalose concentration is between 80 and 100 mg/mL, and wherein said acetate buffer is a 10 mM sodium acetate buffer.

* * * * *

UNITED STATES PATENT AND TRADEMARK OFFICE
CERTIFICATE OF CORRECTION

PATENT NO. : 8,637,021 B2
APPLICATION NO. : 12/740845
DATED : January 28, 2014
INVENTOR(S) : Del Rio et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 196 days.

Signed and Sealed this
Twenty-second Day of September, 2015

Michelle K. Lee
*Director of the United States Patent and Trademark Office*

SEQUENCE LISTING

```
<160> NUMBER OF SEQ ID NOS: 25

<210> SEQ ID NO 1
<211> LENGTH: 166
<212> TYPE: PRT
<213> ORGANISM: homo sapiens
```

-continued

<400> SEQUENCE: 1

Met Ser Gly Leu Gly Arg Ser Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Gly His Arg Gly Ser
    130                 135                 140

Glu Ala Ser Pro Ala Leu Pro Gly Leu Lys Leu Ser Ala Asn Gln Val
145                 150                 155                 160

Ala Leu Val Tyr Ser Thr
                165

<210> SEQ ID NO 2
<211> LENGTH: 232
<212> TYPE: PRT
<213> ORGANISM: homo sapiens

<400> SEQUENCE: 2

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

```
Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 3
<211> LENGTH: 313
<212> TYPE: PRT
<213> ORGANISM: homo sapiens

<400> SEQUENCE: 3

Ala Met Arg Ser Cys Pro Glu Glu Gln Tyr Trp Asp Pro Leu Leu Gly
1               5                   10                  15

Thr Cys Met Ser Cys Lys Thr Ile Cys Asn His Gln Ser Gln Arg Thr
            20                  25                  30

Cys Ala Ala Phe Cys Arg Ser Leu Ser Cys Arg Lys Glu Gln Gly Lys
        35                  40                  45

Phe Tyr Asp His Leu Leu Arg Asp Cys Ile Ser Cys Ala Ser Ile Cys
50                  55                  60

Gly Gln His Pro Lys Gln Cys Ala Tyr Phe Cys Glu Asn Lys Leu Arg
65                  70                  75                  80

Ser Glu Pro Lys Ser Ser Asp Lys Thr His Thr Cys Pro Pro Cys Pro
                85                  90                  95

Ala Pro Glu Ala Glu Gly Ala Pro Ser Val Phe Leu Phe Pro Pro Lys
            100                 105                 110

Pro Lys Asp Thr Leu Met Ile Ser Arg Thr Pro Glu Val Thr Cys Val
        115                 120                 125

Val Val Asp Val Ser His Glu Asp Pro Glu Val Lys Phe Asn Trp Tyr
130                 135                 140

Val Asp Gly Val Glu Val His Asn Ala Lys Thr Lys Pro Arg Glu Glu
145                 150                 155                 160

Gln Tyr Asn Ser Thr Tyr Arg Val Val Ser Val Leu Thr Val Leu His
                165                 170                 175

Gln Asp Trp Leu Asn Gly Lys Glu Tyr Lys Cys Lys Val Ser Asn Lys
            180                 185                 190

Ala Leu Pro Ser Ser Ile Glu Lys Thr Ile Ser Lys Ala Lys Gly Gln
        195                 200                 205

Pro Arg Glu Pro Gln Val Tyr Thr Leu Pro Pro Ser Arg Asp Glu Leu
210                 215                 220

Thr Lys Asn Gln Val Ser Leu Thr Cys Leu Val Lys Gly Phe Tyr Pro
225                 230                 235                 240

Ser Asp Ile Ala Val Glu Trp Glu Ser Asn Gly Gln Pro Glu Asn Asn
                245                 250                 255

Tyr Lys Thr Thr Pro Pro Val Leu Asp Ser Asp Gly Ser Phe Phe Leu
            260                 265                 270

Tyr Ser Lys Leu Thr Val Asp Lys Ser Arg Trp Gln Gln Gly Asn Val
        275                 280                 285

Phe Ser Cys Ser Val Met His Glu Ala Leu His Asn His Tyr Thr Gln
290                 295                 300

Lys Ser Leu Ser Leu Ser Pro Gly Lys
305                 310
```

```
<210> SEQ ID NO 4
<211> LENGTH: 762
<212> TYPE: DNA
<213> ORGANISM: homo sapiens
<220> FEATURE:
<221> NAME/KEY: CDS
<222> LOCATION: (7)..(759)

<400> SEQUENCE: 4 ggatcc atg aag cac ctg tgg ttc ttc ctc ctg ctg gtg gcg gct ccc         48
       Met Lys His Leu Trp Phe Phe Leu Leu Leu Val Ala Ala Pro
       1               5                   10 aga tgg gtc ctg tcc gag ccc aaa tct tgt gac aaa act cac aca tgc        96
Arg Trp Val Leu Ser Glu Pro Lys Ser Cys Asp Lys Thr His Thr Cys
15                  20                  25                  30 cca ccg tgc cca gca cct gaa ctc ctg ggg gga ccg tca gtc ttc ctc       144
Pro Pro Cys Pro Ala Pro Glu Leu Leu Gly Gly Pro Ser Val Phe Leu
                35                  40                  45 ttc ccc cca aaa ccc aag gac acc ctc atg atc tcc cgg acc cct gag       192
Phe Pro Pro Lys Pro Lys Asp Thr Leu Met Ile Ser Arg Thr Pro Glu
    50                  55                  60 gtc aca tgc gtg gtg gtg gac gtg agc cac gaa gac cct gag gtc aag       240
Val Thr Cys Val Val Val Asp Val Ser His Glu Asp Pro Glu Val Lys
65                  70                  75 ttc aac tgg tac gtg gac ggc gtg gag gtg cat aat gcc aag aca aag       288
Phe Asn Trp Tyr Val Asp Gly Val Glu Val His Asn Ala Lys Thr Lys
            80                  85                  90 ccg cgg gag gag cag tac aac agc acg tac cgt gtg gtc agc gtc ctc       336
Pro Arg Glu Glu Gln Tyr Asn Ser Thr Tyr Arg Val Val Ser Val Leu
95                  100                 105                 110 acc gtc ctg cac cag gac tgg ctg aat ggc aag gag tac aag tgc aag       384
Thr Val Leu His Gln Asp Trp Leu Asn Gly Lys Glu Tyr Lys Cys Lys
                115                 120                 125 gtc tcc aac aaa gcc ctc cca gcc ccc atc gag aaa acc atc tcc aaa       432
Val Ser Asn Lys Ala Leu Pro Ala Pro Ile Glu Lys Thr Ile Ser Lys
    130                 135                 140 gcc aaa ggg cag ccc cga gaa cca cag gtg tac acc ctg ccc cca tcc       480
Ala Lys Gly Gln Pro Arg Glu Pro Gln Val Tyr Thr Leu Pro Pro Ser
145                 150                 155 cgg gat gag ctg acc aag aac cag gtc agc ctg acc tgc ctg gtc aaa       528
Arg Asp Glu Leu Thr Lys Asn Gln Val Ser Leu Thr Cys Leu Val Lys
            160                 165                 170 ggc ttc tat ccc agc gac atc gcc gtg gag tgg gag agc aat ggg cag       576
Gly Phe Tyr Pro Ser Asp Ile Ala Val Glu Trp Glu Ser Asn Gly Gln
175                 180                 185                 190 ccg gag aac aac tac aag acc acg cct ccc gtg ctg gac tcc gac ggc       624
Pro Glu Asn Asn Tyr Lys Thr Thr Pro Pro Val Leu Asp Ser Asp Gly
                195                 200                 205 tcc ttc ttc ctc tac agc aag ctc acc gtg gac aag agc agg tgg cag       672
Ser Phe Phe Leu Tyr Ser Lys Leu Thr Val Asp Lys Ser Arg Trp Gln
    210                 215                 220 cag ggg aac gtc ttc tca tgc tcc gtg atg cat gag gct ctg cac aac       720
Gln Gly Asn Val Phe Ser Cys Ser Val Met His Glu Ala Leu His Asn
225                 230                 235 cac tac acg cag aag agc ctc tcc ctg tct ccg ggt aaa tga              762
His Tyr Thr Gln Lys Ser Leu Ser Leu Ser Pro Gly Lys
            240                 245                 250

<210> SEQ ID NO 5
<211> LENGTH: 251
<212> TYPE: PRT
<213> ORGANISM: homo sapiens
```

-continued

```
<400> SEQUENCE: 5

Met Lys His Leu Trp Phe Phe Leu Leu Leu Val Ala Ala Pro Arg Trp
1               5                   10                  15

Val Leu Ser Glu Pro Lys Ser Cys Asp Lys Thr His Thr Cys Pro Pro
            20                  25                  30

Cys Pro Ala Pro Glu Leu Leu Gly Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250

<210> SEQ ID NO 6
<211> LENGTH: 293
<212> TYPE: PRT
<213> ORGANISM: homo sapiens

<400> SEQUENCE: 6

Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110
```

```
Asn Leu Pro Pro Glu Leu Arg Arg Gln Arg Ser Gly Glu Val Glu Asn
        115                 120                 125
Asn Ser Asp Asn Ser Gly Arg Tyr Gln Gly Leu Glu His Arg Gly Ser
    130                 135                 140
Glu Ala Ser Pro Ala Leu Pro Gly Leu Lys Leu Ser Ala Asp Gln Val
145                 150                 155                 160
Ala Leu Val Tyr Ser Thr Leu Gly Leu Cys Leu Cys Ala Val Leu Cys
                165                 170                 175
Cys Phe Leu Val Ala Val Ala Cys Phe Leu Lys Lys Arg Gly Asp Pro
            180                 185                 190
Cys Ser Cys Gln Pro Arg Ser Arg Pro Arg Gln Ser Pro Ala Lys Ser
        195                 200                 205
Ser Gln Asp His Ala Met Glu Ala Gly Ser Pro Val Ser Thr Ser Pro
    210                 215                 220
Glu Pro Val Glu Thr Cys Ser Phe Cys Phe Pro Glu Cys Arg Ala Pro
225                 230                 235                 240
Thr Gln Glu Ser Ala Val Thr Pro Gly Thr Pro Asp Pro Thr Cys Ala
                245                 250                 255
Gly Arg Trp Gly Cys His Thr Arg Thr Thr Val Leu Gln Pro Cys Pro
            260                 265                 270
His Ile Pro Asp Ser Gly Leu Gly Ile Val Cys Val Pro Ala Gln Glu
        275                 280                 285
Gly Gly Pro Gly Ala
        290

<210> SEQ ID NO 7
<211> LENGTH: 1214
<212> TYPE: DNA
<213> ORGANISM: homo sapiens
<220> FEATURE:
<221> NAME/KEY: CDS
<222> LOCATION: (17)..(1192)

<400> SEQUENCE: 7
tattaggccg gccacc atg gat gca atg aag aga ggg ctc tgc tgt gtg ctg      52
               Met Asp Ala Met Lys Arg Gly Leu Cys Cys Val Leu
                 1               5                  10 ctg ctg tgt ggc gcc gtc ttc gtt tcg ctc agc cag gaa atc cat gcc       100
Leu Leu Cys Gly Ala Val Phe Val Ser Leu Ser Gln Glu Ile His Ala
            15                  20                  25 gag ttg aga cgc ttc cgt aga gct atg aga tcc tgc ccc gaa gag cag       148
Glu Leu Arg Arg Phe Arg Arg Ala Met Arg Ser Cys Pro Glu Glu Gln
    30                  35                  40 tac tgg gat cct ctg ctg ggt acc tgc atg tcc tgc aaa acc att tgc       196
Tyr Trp Asp Pro Leu Leu Gly Thr Cys Met Ser Cys Lys Thr Ile Cys
45                  50                  55                  60 aac cat cag agc cag cgc acc tgt gca gcc ttc tgc agg tca ctc agc       244
Asn His Gln Ser Gln Arg Thr Cys Ala Ala Phe Cys Arg Ser Leu Ser
                65                  70                  75 tgc cgc aag gag caa ggc aag ttc tat gac cat ctc ctg agg gac tgc       292
Cys Arg Lys Glu Gln Gly Lys Phe Tyr Asp His Leu Leu Arg Asp Cys
            80                  85                  90 atc agc tgt gcc tcc atc tgt gga cag cac cct aag caa tgt gca tac       340
Ile Ser Cys Ala Ser Ile Cys Gly Gln His Pro Lys Gln Cys Ala Tyr
        95                  100                 105 ttc tgt gag aac aag ctc agg agc cca gtg aac ctt cca cca gag ctc       388
Phe Cys Glu Asn Lys Leu Arg Ser Pro Val Asn Leu Pro Pro Glu Leu
    110                 115                 120
```

```
agg aga cag cgg agt gga gaa gtt gaa aac aat tca gac aac tcg gga        436
Arg Arg Gln Arg Ser Gly Glu Val Glu Asn Asn Ser Asp Asn Ser Gly
125                 130                 135                 140 agg tac caa gga ttg gag cac aga ggc tca gaa gca agt cca gct ctc        484
Arg Tyr Gln Gly Leu Glu His Arg Gly Ser Glu Ala Ser Pro Ala Leu
                145                 150                 155 cca ggt ctc aag gag ccc aaa tct tca gac aaa act cac aca tgc cca        532
Pro Gly Leu Lys Glu Pro Lys Ser Ser Asp Lys Thr His Thr Cys Pro
            160                 165                 170 ccg tgc cca gca cct gaa gcc gag ggg gca ccg tca gtc ttc ctc ttc        580
Pro Cys Pro Ala Pro Glu Ala Glu Gly Ala Pro Ser Val Phe Leu Phe
        175                 180                 185 ccc cca aaa ccc aag gac acc ctc atg atc tcc cgg acc cct gag gtc        628
Pro Pro Lys Pro Lys Asp Thr Leu Met Ile Ser Arg Thr Pro Glu Val
    190                 195                 200 aca tgc gtg gtg gtg gac gtg agc cac gaa gac cct gag gtc aag ttc        676
Thr Cys Val Val Val Asp Val Ser His Glu Asp Pro Glu Val Lys Phe
205                 210                 215                 220 aac tgg tac gtg gac ggc gtg gag gtg cat aat gcc aag aca aag ccg        724
Asn Trp Tyr Val Asp Gly Val Glu Val His Asn Ala Lys Thr Lys Pro
                225                 230                 235 cgg gag gag cag tac aac agc acg tac cgt gtg gtc agc gtc ctc acc        772
Arg Glu Glu Gln Tyr Asn Ser Thr Tyr Arg Val Val Ser Val Leu Thr
            240                 245                 250 gtc ctg cac cag gac tgg ctg aat ggc aag gag tac aag tgc aag gtc        820
Val Leu His Gln Asp Trp Leu Asn Gly Lys Glu Tyr Lys Cys Lys Val
        255                 260                 265 tcc aac aaa gcc ctc cca tcc tcc atc gag aaa acc atc tcc aaa gcc        868
Ser Asn Lys Ala Leu Pro Ser Ser Ile Glu Lys Thr Ile Ser Lys Ala
    270                 275                 280 aaa ggg cag ccc cga gaa cca cag gtg tac acc ctg ccc cca tcc cgg        916
Lys Gly Gln Pro Arg Glu Pro Gln Val Tyr Thr Leu Pro Pro Ser Arg
285                 290                 295                 300 gat gag ctg acc aag aac cag gtc agc ctg acc tgc ctg gtc aaa ggc        964
Asp Glu Leu Thr Lys Asn Gln Val Ser Leu Thr Cys Leu Val Lys Gly
                305                 310                 315 ttc tat ccc agc gac atc gcc gtg gag tgg gag agc aat ggg cag ccg       1012
Phe Tyr Pro Ser Asp Ile Ala Val Glu Trp Glu Ser Asn Gly Gln Pro
            320                 325                 330 gag aac aac tac aag acc acg cct ccc gtg ctg gac tcc gac ggc tcc       1060
Glu Asn Asn Tyr Lys Thr Thr Pro Pro Val Leu Asp Ser Asp Gly Ser
        335                 340                 345 ttc ttc ctc tac agc aag ctc acc gtg gac aag agc agg tgg cag cag       1108
Phe Phe Leu Tyr Ser Lys Leu Thr Val Asp Lys Ser Arg Trp Gln Gln
    350                 355                 360 ggg aac gtc ttc tca tgc tcc gtg atg cat gag gct ctg cac aac cac       1156
Gly Asn Val Phe Ser Cys Ser Val Met His Glu Ala Leu His Asn His
365                 370                 375                 380 tac acg cag aag agc ctc tcc ctg tct ccg ggt aaa taatctagag            1202
Tyr Thr Gln Lys Ser Leu Ser Leu Ser Pro Gly Lys
                385                 390 gcgcgccaat ta                                                         1214

<210> SEQ ID NO 8
<211> LENGTH: 392
<212> TYPE: PRT
<213> ORGANISM: homo sapiens
```

<400> SEQUENCE: 8

```
Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ala Met Arg Ser Cys Pro Glu Glu Gln Tyr Trp Asp Pro
        35                  40                  45

Leu Leu Gly Thr Cys Met Ser Cys Lys Thr Ile Cys Asn His Gln Ser
50                  55                  60

Gln Arg Thr Cys Ala Ala Phe Cys Arg Ser Leu Ser Cys Arg Lys Glu
65                  70                  75                  80

Gln Gly Lys Phe Tyr Asp His Leu Leu Arg Asp Cys Ile Ser Cys Ala
            85                  90                  95

Ser Ile Cys Gly Gln His Pro Lys Gln Cys Ala Tyr Phe Cys Glu Asn
            100                 105                 110

Lys Leu Arg Ser Pro Val Asn Leu Pro Pro Glu Leu Arg Arg Gln Arg
        115                 120                 125

Ser Gly Glu Val Glu Asn Asn Ser Asp Asn Ser Gly Arg Tyr Gln Gly
130                 135                 140

Leu Glu His Arg Gly Ser Glu Ala Ser Pro Ala Leu Pro Gly Leu Lys
145                 150                 155                 160

Glu Pro Lys Ser Ser Asp Lys Thr His Thr Cys Pro Pro Cys Pro Ala
            165                 170                 175

Pro Glu Ala Glu Gly Ala Pro Ser Val Phe Leu Phe Pro Pro Lys Pro
        180                 185                 190

Lys Asp Thr Leu Met Ile Ser Arg Thr Pro Glu Val Thr Cys Val Val
        195                 200                 205

Val Asp Val Ser His Glu Asp Pro Glu Val Lys Phe Asn Trp Tyr Val
210                 215                 220

Asp Gly Val Glu Val His Asn Ala Lys Thr Lys Pro Arg Glu Glu Gln
225                 230                 235                 240

Tyr Asn Ser Thr Tyr Arg Val Val Ser Val Leu Thr Val Leu His Gln
            245                 250                 255

Asp Trp Leu Asn Gly Lys Glu Tyr Lys Cys Lys Val Ser Asn Lys Ala
        260                 265                 270

Leu Pro Ser Ser Ile Glu Lys Thr Ile Ser Lys Ala Lys Gly Gln Pro
        275                 280                 285

Arg Glu Pro Gln Val Tyr Thr Leu Pro Pro Ser Arg Asp Glu Leu Thr
290                 295                 300

Lys Asn Gln Val Ser Leu Thr Cys Leu Val Lys Gly Phe Tyr Pro Ser
305                 310                 315                 320

Asp Ile Ala Val Glu Trp Glu Ser Asn Gly Gln Pro Glu Asn Asn Tyr
            325                 330                 335

Lys Thr Thr Pro Pro Val Leu Asp Ser Asp Gly Ser Phe Phe Leu Tyr
        340                 345                 350

Ser Lys Leu Thr Val Asp Lys Ser Arg Trp Gln Gln Gly Asn Val Phe
        355                 360                 365

Ser Cys Ser Val Met His Glu Ala Leu His Asn His Tyr Thr Gln Lys
370                 375                 380

Ser Leu Ser Leu Ser Pro Gly Lys
385                 390
```

```
<210> SEQ ID NO 9
<211> LENGTH: 1070
<212> TYPE: DNA
<213> ORGANISM: homo sapiens
<220> FEATURE:
<221> NAME/KEY: CDS
<222> LOCATION: (17)..(1048)

<400> SEQUENCE: 9
tattaggccg gccacc atg gat gca atg aag aga ggg ctc tgc tgt gtg ctg        52
               Met Asp Ala Met Lys Arg Gly Leu Cys Cys Val Leu
                 1               5                  10 ctg ctg tgt ggc gcc gtc ttc gtt tcg ctc agc cag gaa atc cat gcc         100
Leu Leu Cys Gly Ala Val Phe Val Ser Leu Ser Gln Glu Ile His Ala
         15                  20                  25 gag ttg aga cgc ttc cgt aga gct atg aga tcc tgc ccc gaa gag cag         148
Glu Leu Arg Arg Phe Arg Arg Ala Met Arg Ser Cys Pro Glu Glu Gln
     30                  35                  40 tac tgg gat cct ctg ctg ggt acc tgc atg tcc tgc aaa acc att tgc         196
Tyr Trp Asp Pro Leu Leu Gly Thr Cys Met Ser Cys Lys Thr Ile Cys
 45                  50                  55                  60 aac cat cag agc cag cgc acc tgt gca gcc ttc tgc agg tca ctc agc         244
Asn His Gln Ser Gln Arg Thr Cys Ala Ala Phe Cys Arg Ser Leu Ser
                 65                  70                  75 tgc cgc aag gag caa ggc aag ttc tat gac cat ctc ctg agg gac tgc         292
Cys Arg Lys Glu Gln Gly Lys Phe Tyr Asp His Leu Leu Arg Asp Cys
         80                  85                  90 atc agc tgt gcc tcc atc tgt gga cag cac cct aag caa tgt gca tac         340
Ile Ser Cys Ala Ser Ile Cys Gly Gln His Pro Lys Gln Cys Ala Tyr
     95                 100                 105 ttc tgt gag aac gag ccc aaa tct tca gac aaa act cac aca tgc cca         388
Phe Cys Glu Asn Glu Pro Lys Ser Ser Asp Lys Thr His Thr Cys Pro
110                 115                 120 ccg tgc cca gca cct gaa gcc gag ggg gca ccg tca gtc ttc ctc ttc         436
Pro Cys Pro Ala Pro Glu Ala Glu Gly Ala Pro Ser Val Phe Leu Phe
125                 130                 135                 140 ccc cca aaa ccc aag gac acc ctc atg atc tcc cgg acc cct gag gtc         484
Pro Pro Lys Pro Lys Asp Thr Leu Met Ile Ser Arg Thr Pro Glu Val
                145                 150                 155 aca tgc gtg gtg gtg gac gtg agc cac gaa gac cct gag gtc aag ttc         532
Thr Cys Val Val Val Asp Val Ser His Glu Asp Pro Glu Val Lys Phe
        160                 165                 170 aac tgg tac gtg gac ggc gtg gag gtg cat aat gcc aag aca aag ccg         580
Asn Trp Tyr Val Asp Gly Val Glu Val His Asn Ala Lys Thr Lys Pro
    175                 180                 185 cgg gag gag cag tac aac agc acg tac cgt gtg gtc agc gtc ctc acc         628
Arg Glu Glu Gln Tyr Asn Ser Thr Tyr Arg Val Val Ser Val Leu Thr
190                 195                 200 gtc ctg cac cag gac tgg ctg aat ggc aag gag tac aag tgc aag gtc         676
Val Leu His Gln Asp Trp Leu Asn Gly Lys Glu Tyr Lys Cys Lys Val
205                 210                 215                 220 tcc aac aaa gcc ctc cca tcc tcc atc gag aaa acc atc tcc aaa gcc         724
Ser Asn Lys Ala Leu Pro Ser Ser Ile Glu Lys Thr Ile Ser Lys Ala
                225                 230                 235 aaa ggg cag ccc cga gaa cca cag gtg tac acc ctg ccc cca tcc cgg         772
Lys Gly Gln Pro Arg Glu Pro Gln Val Tyr Thr Leu Pro Pro Ser Arg
        240                 245                 250 gat gag ctg acc aag aac cag gtc agc ctg acc tgc ctg gtc aaa ggc         820
Asp Glu Leu Thr Lys Asn Gln Val Ser Leu Thr Cys Leu Val Lys Gly
    255                 260                 265
```

```
ttc tat ccc agc gac atc gcc gtg gag tgg gag agc aat ggg cag ccg     868
Phe Tyr Pro Ser Asp Ile Ala Val Glu Trp Glu Ser Asn Gly Gln Pro
    270             275                 280 gag aac aac tac aag acc acg cct ccc gtg ctg gac tcc gac ggc tcc     916
Glu Asn Asn Tyr Lys Thr Thr Pro Pro Val Leu Asp Ser Asp Gly Ser
285                 290                 295                 300 ttc ttc ctc tac agc aag ctc acc gtg gac aag agc agg tgg cag cag     964
Phe Phe Leu Tyr Ser Lys Leu Thr Val Asp Lys Ser Arg Trp Gln Gln
                305                 310                 315 ggg aac gtc ttc tca tgc tcc gtg atg cat gag gct ctg cac aac cac    1012
Gly Asn Val Phe Ser Cys Ser Val Met His Glu Ala Leu His Asn His
            320                 325                 330 tac acg cag aag agc ctc tcc ctg tct ccg ggt aaa taatctagag         1058
Tyr Thr Gln Lys Ser Leu Ser Leu Ser Pro Gly Lys
        335                 340 gcgcgccaat ta                                                      1070

<210> SEQ ID NO 10
<211> LENGTH: 344
<212> TYPE: PRT
<213> ORGANISM: homo sapiens

<400> SEQUENCE: 10

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ala Met Arg Ser Cys Pro Glu Glu Gln Tyr Trp Asp Pro
        35                  40                  45

Leu Leu Gly Thr Cys Met Ser Cys Lys Thr Ile Cys Asn His Gln Ser
    50                  55                  60

Gln Arg Thr Cys Ala Ala Phe Cys Arg Ser Leu Ser Cys Arg Lys Glu
65                  70                  75                  80

Gln Gly Lys Phe Tyr Asp His Leu Leu Arg Asp Cys Ile Ser Cys Ala
                85                  90                  95

Ser Ile Cys Gly Gln His Pro Lys Gln Cys Ala Tyr Phe Cys Glu Asn
            100                 105                 110

Glu Pro Lys Ser Ser Asp Lys Thr His Thr Cys Pro Pro Cys Pro Ala
        115                 120                 125

Pro Glu Ala Glu Gly Ala Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Ser Ser Ile Glu Lys Thr Ile Ser Lys Ala Lys Gly Gln Pro
225                 230                 235                 240

Arg Glu Pro Gln Val Tyr Thr Leu Pro Pro Ser Arg Asp Glu Leu Thr
                245                 250                 255

Lys Asn Gln Val Ser Leu Thr Cys Leu Val Lys Gly Phe Tyr Pro Ser
            260                 265                 270
```

```
Asp Ile Ala Val Glu Trp Glu Ser Asn Gly Gln Pro Glu Asn Asn Tyr
            275                 280                 285

Lys Thr Thr Pro Pro Val Leu Asp Ser Asp Gly Ser Phe Phe Leu Tyr
290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 11
<211> LENGTH: 1082
<212> TYPE: DNA
<213> ORGANISM: homo sapiens
<220> FEATURE:
<221> NAME/KEY: CDS
<222> LOCATION: (17)..(1060)

<400> SEQUENCE: 11
tattaggccg gccacc atg gat gca atg aag aga ggg ctc tgc tgt gtg ctg    52
                 Met Asp Ala Met Lys Arg Gly Leu Cys Cys Val Leu
                  1               5                  10 ctg ctg tgt ggc gcc gtc ttc gtt tcg ctc agc cag gaa atc cat gcc    100
Leu Leu Cys Gly Ala Val Phe Val Ser Leu Ser Gln Glu Ile His Ala
         15                  20                  25 gag ttg aga cgc ttc cgt aga gct atg aga tcc tgc ccc gaa gag cag    148
Glu Leu Arg Arg Phe Arg Arg Ala Met Arg Ser Cys Pro Glu Glu Gln
 30                  35                  40 tac tgg gat cct ctg ctg ggt acc tgc atg tcc tgc aaa acc att tgc    196
Tyr Trp Asp Pro Leu Leu Gly Thr Cys Met Ser Cys Lys Thr Ile Cys
45                  50                  55                  60 aac cat cag agc cag cgc acc tgt gca gcc ttc tgc agg tca ctc agc    244
Asn His Gln Ser Gln Arg Thr Cys Ala Ala Phe Cys Arg Ser Leu Ser
                 65                  70                  75 tgc cgc aag gag caa ggc aag ttc tat gac cat ctc ctg agg gac tgc    292
Cys Arg Lys Glu Gln Gly Lys Phe Tyr Asp His Leu Leu Arg Asp Cys
         80                  85                  90 atc agc tgt gcc tcc atc tgt gga cag cac cct aag caa tgt gca tac    340
Ile Ser Cys Ala Ser Ile Cys Gly Gln His Pro Lys Gln Cys Ala Tyr
 95                 100                 105 ttc tgt gag aac aag ctc agg agc gag ccc aaa tct tca gac aaa act    388
Phe Cys Glu Asn Lys Leu Arg Ser Glu Pro Lys Ser Ser Asp Lys Thr
110                 115                 120 cac aca tgc cca ccg tgc cca gca cct gaa gcc gag ggg gca ccg tca    436
His Thr Cys Pro Pro Cys Pro Ala Pro Glu Ala Glu Gly Ala Pro Ser
125                 130                 135                 140 gtc ttc ctc ttc ccc cca aaa ccc aag gac acc ctc atg atc tcc cgg    484
Val Phe Leu Phe Pro Pro Lys Pro Lys Asp Thr Leu Met Ile Ser Arg
                145                 150                 155 acc cct gag gtc aca tgc gtg gtg gtg gac gtg agc cac gaa gac cct    532
Thr Pro Glu Val Thr Cys Val Val Val Asp Val Ser His Glu Asp Pro
         160                 165                 170 gag gtc aag ttc aac tgg tac gtg gac ggc gtg gag gtg cat aat gcc    580
Glu Val Lys Phe Asn Trp Tyr Val Asp Gly Val Glu Val His Asn Ala
175                 180                 185 aag aca aag ccg cgg gag gag cag tac aac agc acg tac cgt gtg gtc    628
Lys Thr Lys Pro Arg Glu Glu Gln Tyr Asn Ser Thr Tyr Arg Val Val
190                 195                 200
```

```
agc gtc ctc acc gtg ctg cac cag gac tgg ctg aat ggc aag gag tac      676
Ser Val Leu Thr Val Leu His Gln Asp Trp Leu Asn Gly Lys Glu Tyr
205                 210                 215                 220 aag tgc aag gtc tcc aac aaa gcc ctc cca tcc tcc atc gag aaa acc      724
Lys Cys Lys Val Ser Asn Lys Ala Leu Pro Ser Ser Ile Glu Lys Thr
                225                 230                 235 atc tcc aaa gcc aaa ggg cag ccc cga gaa cca cag gtg tac acc ctg      772
Ile Ser Lys Ala Lys Gly Gln Pro Arg Glu Pro Gln Val Tyr Thr Leu
    240                 245                 250 ccc cca tcc cgg gat gag ctg acc aag aac cag gtc agc ctg acc tgc      820
Pro Pro Ser Arg Asp Glu Leu Thr Lys Asn Gln Val Ser Leu Thr Cys
255                 260                 265 ctg gtc aaa ggc ttc tat ccc agc gac atc gcc gtg gag tgg gag agc      868
Leu Val Lys Gly Phe Tyr Pro Ser Asp Ile Ala Val Glu Trp Glu Ser
    270                 275                 280 aat ggg cag ccg gag aac aac tac aag acc acg cct ccc gtg ctg gac      916
Asn Gly Gln Pro Glu Asn Asn Tyr Lys Thr Thr Pro Pro Val Leu Asp
285                 290                 295                 300 tcc gac ggc tcc ttc ttc ctc tac agc aag ctc acc gtg gac aag agc      964
Ser Asp Gly Ser Phe Phe Leu Tyr Ser Lys Leu Thr Val Asp Lys Ser
                305                 310                 315 agg tgg cag cag ggg aac gtc ttc tca tgc tcc gtg atg cat gag gct     1012
Arg Trp Gln Gln Gly Asn Val Phe Ser Cys Ser Val Met His Glu Ala
                320                 325                 330 ctg cac aac cac tac acg cag aag agc ctc tcc ctg tct ccg ggt aaa     1060
Leu His Asn His Tyr Thr Gln Lys Ser Leu Ser Leu Ser Pro Gly Lys
            335                 340                 345 taatctagag gcgcgccaat ta                                             1082

<210> SEQ ID NO 12
<211> LENGTH: 348
<212> TYPE: PRT
<213> ORGANISM: homo sapiens

<400> SEQUENCE: 12

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
                20                  25                  30

Phe Arg Arg Ala Met Arg Ser Cys Pro Glu Glu Gln Tyr Trp Asp Pro
            35                  40                  45

Leu Leu Gly Thr Cys Met Ser Cys Lys Thr Ile Cys Asn His Gln Ser
        50                  55                  60

Gln Arg Thr Cys Ala Ala Phe Cys Arg Ser Leu Ser Cys Arg Lys Glu
65                  70                  75                  80

Gln Gly Lys Phe Tyr Asp His Leu Leu Arg Asp Cys Ile Ser Cys Ala
                85                  90                  95

Ser Ile Cys Gly Gln His Pro Lys Gln Cys Ala Tyr Phe Cys Glu Asn
            100                 105                 110

Lys Leu Arg Ser Glu Pro Lys Ser Ser Asp Lys Thr His Thr Cys Pro
        115                 120                 125

Pro Cys Pro Ala Pro Glu Ala Glu Gly Ala Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175
```

-continued

```
Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
            195                 200                 205

Val Leu His Gln Asp Trp Leu Asn Gly Lys Glu Tyr Lys Cys Lys Val
        210                 215                 220

Ser Asn Lys Ala Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Asp Glu Leu Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345

<210> SEQ ID NO 13
<211> LENGTH: 1109
<212> TYPE: DNA
<213> ORGANISM: homo sapiens
<220> FEATURE:
<221> NAME/KEY: CDS
<222> LOCATION: (17)..(1090)

<400> SEQUENCE: 13
tattaggccg gccacc atg gat gca atg aag aga ggg ctc tgc tgt gtg ctg      52
                Met Asp Ala Met Lys Arg Gly Leu Cys Cys Val Leu
                  1               5                  10 ctg ctg tgt ggc gcc gtc ttc gtt tcg ctc agc cag gaa atc cat gcc      100
Leu Leu Cys Gly Ala Val Phe Val Ser Leu Ser Gln Glu Ile His Ala
         15                  20                  25 gag ttg aga cgc ttc cgt aga gct atg aga tcc tgc ccc gaa gag cag      148
Glu Leu Arg Arg Phe Arg Arg Ala Met Arg Ser Cys Pro Glu Glu Gln
     30                  35                  40 tac tgg gat cct ctg ctg ggt acc tgc atg tcc tgc aaa acc att tgc      196
Tyr Trp Asp Pro Leu Leu Gly Thr Cys Met Ser Cys Lys Thr Ile Cys
 45                  50                  55                  60 aac cat cag agc cag cgc acc tgt gca gcc ttc tgc agg tca ctc agc      244
Asn His Gln Ser Gln Arg Thr Cys Ala Ala Phe Cys Arg Ser Leu Ser
                 65                  70                  75 tgc cgc aag gag caa ggc aag ttc tat gac cat ctc ctg agg gac tgc      292
Cys Arg Lys Glu Gln Gly Lys Phe Tyr Asp His Leu Leu Arg Asp Cys
             80                  85                  90 atc agc tgt gcc tcc atc tgt gga cag cac cct aag caa tgt gca tac      340
Ile Ser Cys Ala Ser Ile Cys Gly Gln His Pro Lys Gln Cys Ala Tyr
         95                 100                 105 ttc tgt gag aac aag ctc agg agc cca gtg aac ctt cca cca gag ctc      388
Phe Cys Glu Asn Lys Leu Arg Ser Pro Val Asn Leu Pro Pro Glu Leu
    110                 115                 120 agg agg ccc aaa tct tca gac aaa act cac aca tgc cca ccg tgc cca      436
Arg Arg Pro Lys Ser Ser Asp Lys Thr His Thr Cys Pro Pro Cys Pro
125                 130                 135                 140
```

```
gca cct gaa gcc gag ggg gca ccg tca gtc ttc ctc ttc ccc cca aaa    484
Ala Pro Glu Ala Glu Gly Ala Pro Ser Val Phe Leu Phe Pro Pro Lys
            145                 150                 155 ccc aag gac acc ctc atg atc tcc cgg acc cct gag gtc aca tgc gtg    532
Pro Lys Asp Thr Leu Met Ile Ser Arg Thr Pro Glu Val Thr Cys Val
        160                 165                 170 gtg gtg gac gtg agc cac gaa gac cct gag gtc aag ttc aac tgg tac    580
Val Val Asp Val Ser His Glu Asp Pro Glu Val Lys Phe Asn Trp Tyr
    175                 180                 185 gtg gac ggc gtg gag gtg cat aat gcc aag aca aag ccg cgg gag gag    628
Val Asp Gly Val Glu Val His Asn Ala Lys Thr Lys Pro Arg Glu Glu
190                 195                 200 cag tac aac agc acg tac cgt gtg gtc agc gtc ctc acc gtc ctg cac    676
Gln Tyr Asn Ser Thr Tyr Arg Val Val Ser Val Leu Thr Val Leu His
205                 210                 215                 220 cag gac tgg ctg aat ggc aag gag tac aag tgc aag gtc tcc aac aaa    724
Gln Asp Trp Leu Asn Gly Lys Glu Tyr Lys Cys Lys Val Ser Asn Lys
                225                 230                 235 gcc ctc cca tcc tcc atc gag aaa acc atc tcc aaa gcc aaa ggg cag    772
Ala Leu Pro Ser Ser Ile Glu Lys Thr Ile Ser Lys Ala Lys Gly Gln
            240                 245                 250 ccc cga gaa cca cag gtg tac acc ctg ccc cca tcc cgg gat gag ctg    820
Pro Arg Glu Pro Gln Val Tyr Thr Leu Pro Pro Ser Arg Asp Glu Leu
        255                 260                 265 acc aag aac cag gtc agc ctg acc tgc ctg gtc aaa ggc ttc tat ccc    868
Thr Lys Asn Gln Val Ser Leu Thr Cys Leu Val Lys Gly Phe Tyr Pro
    270                 275                 280 agc gac atc gcc gtg gag tgg gag agc aat ggg cag ccg gag aac aac    916
Ser Asp Ile Ala Val Glu Trp Glu Ser Asn Gly Gln Pro Glu Asn Asn
285                 290                 295                 300 tac aag acc acg cct ccc gtg ctg gac tcc gac ggc tcc ttc ttc ctc    964
Tyr Lys Thr Thr Pro Pro Val Leu Asp Ser Asp Gly Ser Phe Phe Leu
                305                 310                 315 tac agc aag ctc acc gtg gac aag agc agg tgg cag cag ggg aac gtc   1012
Tyr Ser Lys Leu Thr Val Asp Lys Ser Arg Trp Gln Gln Gly Asn Val
            320                 325                 330 ttc tca tgc tcc gtg atg cat gag gct ctg cac aac cac tac acg cag   1060
Phe Ser Cys Ser Val Met His Glu Ala Leu His Asn His Tyr Thr Gln
        335                 340                 345 aag agc ctc tcc ctg tct ccg ggt aaa taa tctagaggcg cgccaatta      1109
Lys Ser Leu Ser Leu Ser Pro Gly Lys
    350                 355

<210> SEQ ID NO 14
<211> LENGTH: 357
<212> TYPE: PRT
<213> ORGANISM: homo sapiens

<400> SEQUENCE: 14

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ala Met Arg Ser Cys Pro Glu Glu Gln Tyr Trp Asp Pro
        35                  40                  45

Leu Leu Gly Thr Cys Met Ser Cys Lys Thr Ile Cys Asn His Gln Ser
    50                  55                  60

Gln Arg Thr Cys Ala Ala Phe Cys Arg Ser Leu Ser Cys Arg Lys Glu
65                  70                  75                  80
```

```
Gln Gly Lys Phe Tyr Asp His Leu Leu Arg Asp Cys Ile Ser Cys Ala
                85                  90                  95
Ser Ile Cys Gly Gln His Pro Lys Gln Cys Ala Tyr Phe Cys Glu Asn
            100                 105                 110
Lys Leu Arg Ser Pro Val Asn Leu Pro Pro Glu Leu Arg Glu Pro Lys
        115                 120                 125
Ser Ser Asp Lys Thr His Thr Cys Pro Pro Cys Pro Ala Pro Glu Ala
130                 135                 140
Glu Gly Ala Pro Ser Val Phe Leu Phe Pro Pro Lys Pro Lys Asp Thr
145                 150                 155                 160
Leu Met Ile Ser Arg Thr Pro Glu Val Thr Cys Val Val Val Asp Val
                165                 170                 175
Ser His Glu Asp Pro Glu Val Lys Phe Asn Trp Tyr Val Asp Gly Val
            180                 185                 190
Glu Val His Asn Ala Lys Thr Lys Pro Arg Glu Glu Gln Tyr Asn Ser
        195                 200                 205
Thr Tyr Arg Val Val Ser Val Leu Thr Val Leu His Gln Asp Trp Leu
210                 215                 220
Asn Gly Lys Glu Tyr Lys Cys Lys Val Ser Asn Lys Ala Leu Pro Ser
225                 230                 235                 240
Ser Ile Glu Lys Thr Ile Ser Lys Ala Lys Gly Gln Pro Arg Glu Pro
                245                 250                 255
Gln Val Tyr Thr Leu Pro Pro Ser Arg Asp Glu Leu Thr Lys Asn Gln
            260                 265                 270
Val Ser Leu Thr Cys Leu Val Lys Gly Phe Tyr Pro Ser Asp Ile Ala
        275                 280                 285
Val Glu Trp Glu Ser Asn Gly Gln Pro Glu Asn Asn Tyr Lys Thr Thr
290                 295                 300
Pro Pro Val Leu Asp Ser Asp Gly Ser Phe Phe Leu Tyr Ser Lys Leu
305                 310                 315                 320
Thr Val Asp Lys Ser Arg Trp Gln Gln Gly Asn Val Phe Ser Cys Ser
                325                 330                 335
Val Met His Glu Ala Leu His Asn His Tyr Thr Gln Lys Ser Leu Ser
            340                 345                 350
Leu Ser Pro Gly Lys
        355
```

<210> SEQ ID NO 15
<211> LENGTH: 29
<212> TYPE: DNA
<213> ORGANISM: artificial sequence
<220> FEATURE:
<223> OTHER INFORMATION: primer sequence

<400> SEQUENCE: 15
tattaggccg gccaccatgg atgcaatga          29

<210> SEQ ID NO 16
<211> LENGTH: 29
<212> TYPE: DNA
<213> ORGANISM: artificial sequence
<220> FEATURE:
<223> OTHER INFORMATION: primer sequence

<400> SEQUENCE: 16
tgaagatttg ggctccttga gacctggga          29

```
<210> SEQ ID NO 17
<211> LENGTH: 29
<212> TYPE: DNA
<213> ORGANISM: artificial sequence
<220> FEATURE:
<223> OTHER INFORMATION: primer sequence

<400> SEQUENCE: 17
tcccaggtct caaggagccc aaatcttca                                      29

<210> SEQ ID NO 18
<211> LENGTH: 36
<212> TYPE: DNA
<213> ORGANISM: artificial sequence
<220> FEATURE:
<223> OTHER INFORMATION: primer sequence

<400> SEQUENCE: 18
taattggcgc gcctctagat tatttacccg gagaca                              36

<210> SEQ ID NO 19
<211> LENGTH: 30
<212> TYPE: DNA
<213> ORGANISM: artificial sequence
<220> FEATURE:
<223> OTHER INFORMATION: primer sequence

<400> SEQUENCE: 19
tgaagatttg ggctcgttct cacagaagta                                     30

<210> SEQ ID NO 20
<211> LENGTH: 31
<212> TYPE: DNA
<213> ORGANISM: artificial sequence
<220> FEATURE:
<223> OTHER INFORMATION: primer sequence

<400> SEQUENCE: 20
atacttctgt gagaacgagc ccaaatcttc a                                   31

<210> SEQ ID NO 21
<211> LENGTH: 30
<212> TYPE: DNA
<213> ORGANISM: artificial sequence
<220> FEATURE:
<223> OTHER INFORMATION: primer sequence

<400> SEQUENCE: 21
tttgggctcg ctcctgagct tgttctcaca                                     30

<210> SEQ ID NO 22
<211> LENGTH: 28
<212> TYPE: DNA
<213> ORGANISM: artificial sequence
<220> FEATURE:
<223> OTHER INFORMATION: primer sequence

<400> SEQUENCE: 22
ctcaggagcg agcccaaatc ttcagaca                                       28

<210> SEQ ID NO 23
<211> LENGTH: 26
<212> TYPE: DNA
<213> ORGANISM: artificial sequence
<220> FEATURE:
<223> OTHER INFORMATION: primer sequence
```

```
<400> SEQUENCE: 23
tttgggctcc ctgagctctg gtggaa                                          26

<210> SEQ ID NO 24
<211> LENGTH: 28
<212> TYPE: DNA
<213> ORGANISM: artificial sequence
<220> FEATURE:
<223> OTHER INFORMATION: primer sequence

<400> SEQUENCE: 24
gagctcaggg agcccaaatc ttcagaca                                        28

<210> SEQ ID NO 25
<211> LENGTH: 35
<212> TYPE: PRT
<213> ORGANISM: artificial sequence
<220> FEATURE:
<223> OTHER INFORMATION: modified signal peptide sequence

<400> SEQUENCE: 25

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg
        35
```